(12) United States Patent
Chen et al.

(10) Patent No.: US 11,160,767 B2
(45) Date of Patent: Nov. 2, 2021

(54) 4,4'-TRANS-DIHYDROXYSTILBENE FOR USE IN TREATING CANCER

(71) Applicant: The George Washington University, a Congressionally Chartered Not-For-Profit Corporation, Washington, DC (US)

(72) Inventors: Chi-Wei Chen, Silver Spring, MD (US); Yongming Li, Liaoning (CN); Zhiyong Han, Fairfax, VA (US); Wenge Zhu, Germantown, MD (US)

(73) Assignee: The George Washington University, a Congressionally Chartered Not-For-Profit Corporation, Washington, DC (US)

( * ) Notice: Subject to any disclaimer, the term of this patent is extended or adjusted under 35 U.S.C. 154(b) by 98 days.

(21) Appl. No.: 16/604,948

(22) PCT Filed: Apr. 11, 2018

(86) PCT No.: PCT/US2018/027086
§ 371 (c)(1),
(2) Date: Oct. 11, 2019

(87) PCT Pub. No.: WO2018/191367
PCT Pub. Date: Oct. 18, 2018

(65) Prior Publication Data
US 2021/0113487 A1    Apr. 22, 2021

Related U.S. Application Data

(60) Provisional application No. 62/484,085, filed on Apr. 11, 2017.

(51) Int. Cl.
| | | |
|---|---|---|
| A61K 31/7064 | (2006.01) | |
| A61K 31/28 | (2006.01) | |
| A61K 31/05 | (2006.01) | |
| A61P 35/00 | (2006.01) | |
| A61K 33/243 | (2019.01) | |
| A61K 45/06 | (2006.01) | |

(52) U.S. Cl.
CPC ............ A61K 31/05 (2013.01); A61K 33/243 (2019.01); A61K 45/06 (2013.01); A61P 35/00 (2018.01)

(58) Field of Classification Search
CPC .... A61K 31/7064; A61K 31/28; A61K 31/17; A61K 31/05; A61P 35/00
USPC .................................. 514/49, 492, 588, 733
See application file for complete search history.

(56) References Cited

U.S. PATENT DOCUMENTS 8,716,355 B2    5/2014    Tsai

FOREIGN PATENT DOCUMENTS

WO    WO-2018191367 A1    10/2018

OTHER PUBLICATIONS

Savio et al., Scientific Reports (2016), 6:19973, pp. 1-12.*
Cai, Y. J., et al., "The 3,4-dihydroxyl groups are important for trans-resveratrol analogs to exhibit enhanced antioxidant and apoptotic activities," *Anticancer Research* 24(2B):999-1002, International Institute of Anticancer Research, Greece (Mar.-Apr. 2004).
Carter, L.G., et al., "Resveratrol and cancer: focus on in vivo evidence," *Endocrine-Related Cancer* 21(3):R209-R225, BioScientifica, United Kingdom (May 2014).
Chen, Z., et al., "Modulation of the ribonucleotide reductase M1-gemcitabine interaction in vivo by N-ethylmaleimide," *Biochemical and Biophysical Research Communications* 413(2):383-388, Elsevier, United States (published online Aug. 2011, published in print Sep. 2011).
Chou, T. C., "Theoretical basis, experimental design, and computerized simulation of synergism and antagonism in drug combination studies," *Pharmacological Reviews* 58(3):621-681, American Society for Pharmacology and Experimental Therapeutics, United States (Sep. 2006).
Cory, J. G., and Sato, A., "Regulation of ribonucleotide reductase activity in mammalian cells," *Molecular and Cellular Biochemistry* 53-54(1-2):257-266, Springer, Netherlands (1983).
D'Angiolella, V., et al., "The cyclin F-mediated degradation of ribonucleotide reductase M2 axis controls genome integrity and DNA repair," *Cell* 149(5):1023-1034, Cell Press, United States (May 2012).
Guittet, O., et al., "Mammalian p53R2 protein forms an active ribonucleotide reductase in vitro with the R1 protein, which is expressed both in resting cells in response to DNA damage and in proliferating cells," *Journal of Biological Chemistry* 276(44):40647-40651, Elsevier Inc., United States (published online Aug. 2001, published in print Nov. 2001).
Hao, J., et al., "And-1 coordinates with Claspin for efficient Chk1 activation in response to replication stress," *The EMBO Journal* 34(15):2096-2110, Wiley Blackwell, United Kingdom (published online Jun. 2015, published in print Aug. 2015).
Hosseini, A., and Ghorbani, A., "Cancer therapy with phytochemicals: evidence from clinical studies," *Avicenna Journal of Phytomedicine* 5(2):84-97, Mashhad University of Medical Sciences, Iran (Mar.-Apr. 2015).
International Search Report and Written Opinion for International Application No. PCT/US18/27086, ISA/US, Alexandria, Virginia, United States, dated Aug. 23, 2018, 10 pages.
Jafari, R., et al., "The cellular thermal shift assay for evaluating drug target interactions in cells," *Nature Protocols* 9(9):2100-2122, Nature Publishing Group, United Kingdom (published online Aug. 2014, published in print Sep. 2014).

(Continued)

*Primary Examiner* — Raymond J Henley, III
(74) *Attorney, Agent, or Firm* — Sterne, Kessler, Goldstein & Fox, P.L.L.C.

(57) ABSTRACT

The present disclosure provides methods, pharmaceutical compositions, dosing regimens, and kits comprising 4,4'-trans-dihydroxystilbene (DHS), including methods of treating cancer in a subject and methods of decreasing or reversing resistance to a DNA damaging agent in a subject.

19 Claims, 25 Drawing Sheets

(56) References Cited

OTHER PUBLICATIONS

Jaramillo-Lambert, A., et al., "Acidic nucleoplasmic DNA-binding protein (And-1) controls chromosome congression by regulating the assembly of centromere protein A (CENP-A) at centromeres," *The Journal of Biological Chemistry* 288(3):1480-1488, Elsevier Inc., United States (published online Nov. 2012, published in print Jan. 2013).

Kohnken, R., et al., "Regulation of deoxynucleotide metabolism in cancer: novel mechanisms and therapeutic implications," *Molecular Cancer* 14:176, BioMed Central, United Kingdom (Sep. 2015).

Li, Y., et al., "And-1 is required for the stability of histone acetyltransferase Gcn5," *Oncogene* 31(5):643-652, Nature Publishing Group, United Kingdom (published online Jul. 2011, published in print Feb. 2012).

Li, Y., et al., "The involvement of acidic nucleoplasmic DNA-binding protein (And-1) in the regulation of prereplicative complex (pre-RC) assembly in human cells," *Journal of Biological Chemistry* 287(51):42469-42479, American Society for Biochemistry and Molecular Biology, United States (published online Oct. 2012, published in print Dec. 2012).

O'Connor, M. J., "Targeting the DNA Damage Response in Cancer," *Molecular Cell* 60(4):547-560, Cell Press, United States (Nov. 2015).

Pangeni, R., et al., "Resveratrol: review on therapeutic potential and recent advances in drug delivery," *Expert Opinion on Drug Delivery* 11(8):1285-1298, Informa Healthcare, United Kingdom (published online May 2014, published in print Aug. 2014).

Plunkett, W., et al., "Preclinical characteristics of gemcitabine," *Anti-Cancer Drugs* 6(Suppl 6):7-13, Lippincott Williams & Wilkins, United Kingdom (Dec. 1995).

Roos, W. P., et al., "DNA damage and the balance between survival and death in cancer biology," *Nature Reviews Cancer* 16(1):20-33, Nature Publishing Group, United Kingdom (published online Dec. 2015, published in print Jan. 2016).

Sato, N., et al., "Activation of WD repeat and high-mobility group box DNA binding protein 1 in pulmonary and esophageal carcinogenesis," *Clinical Cancer Research* 16(1):226-239, The American Association for Cancer Research, United States (published online Dec. 2009, published in print Jan. 2010).

Savio, M., et al., "Resveratrol analogue 4,4'-dihydroxy-trans-stilbene potently inhibits cancer invasion and metastasis," *Scientific Reports* 6:19973, Nature Publishing Group, United Kingdom (Feb. 2016).

Simon, A. C., et al., "A Ctf4 trimer couples the CMG helicase to DNA polymerase α in the eukaryotic replisome," *Nature* 510(7504):293-297, Nature Publishing Group, United Kingdom (published online May 2014, published in print Jun. 2014).

Thelander, M., et al., "Subunit M2 of mammalian ribonucleotide reductase. Characterization of a homogeneous protein isolated from M2-overproducing mouse cells," *Journal of Biological Chemistry* 260(5):2737-2741, American Society for Biochemistry and Molecular Biology, United States (Mar. 1985).

Usha, S., et al., "Modulation of DNA intercalation by resveratrol and genistein," *Molecular and Cellular Biochemistry* 284(1-2):57-64, Springer, Netherlands (Mar. 2006).

Van-Pel, D. M., "*Saccharomyces cerevisiae* genetics predicts candidate therapeutic genetic interactions at the mammalian replication fork," *G3 (Bethesda)* 3(2):273-282, Oxford University Press, United Kingdom (Feb. 2013).

Varoni, E. M., et al., "Anticancer Molecular Mechanisms of Resveratrol," *Frontiers in Nutrition* 3:8, Frontiers Media, Switzerland (Apr. 2016).

Vichai, V., and Kirtikara, K., "Sulforhodamine B colorimetric assay for cytotoxicity screening," *Nature Protocols* 1(3):1112-1116, Nature Publishing Group, United Kingdom (2006).

Zhou, B., et al., "A small-molecule blocking ribonucleotide reductase holoenzyme formation inhibits cancer cell growth and overcomes drug resistance," *Cancer Research* 73(21):6484-6493, American Association for Cancer Research, United States (published online Sep. 2013, published in print Nov. 2013).

\* cited by examiner

Measure Luciferase activity

Seed 2000 cells/well in 1536-well plate

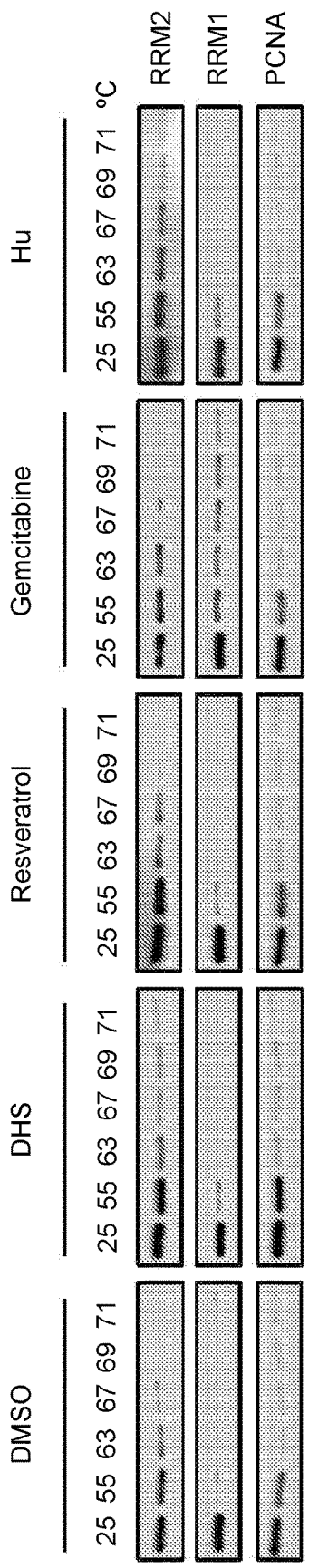
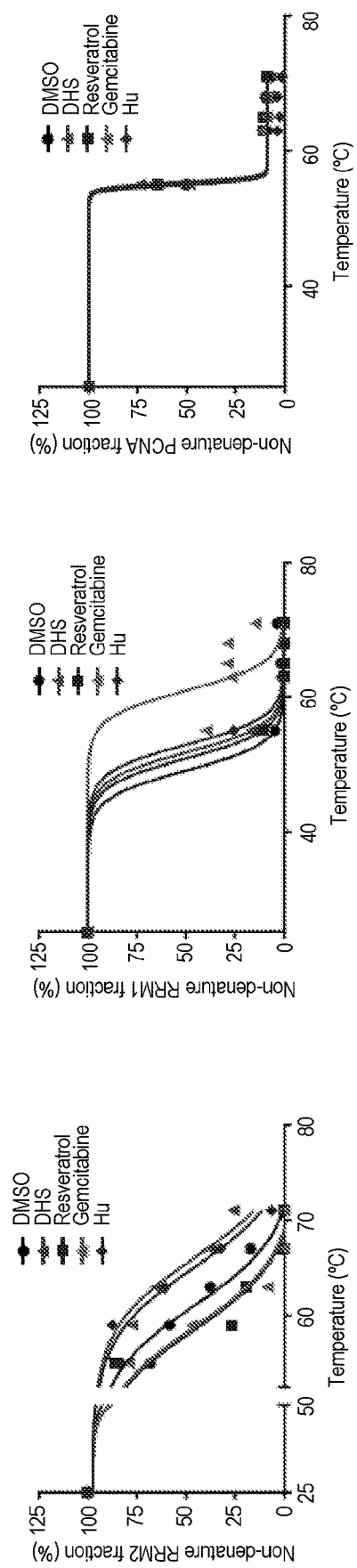
FIG. 10A
FIG. 10B
FIG. 10C
FIG. 10D

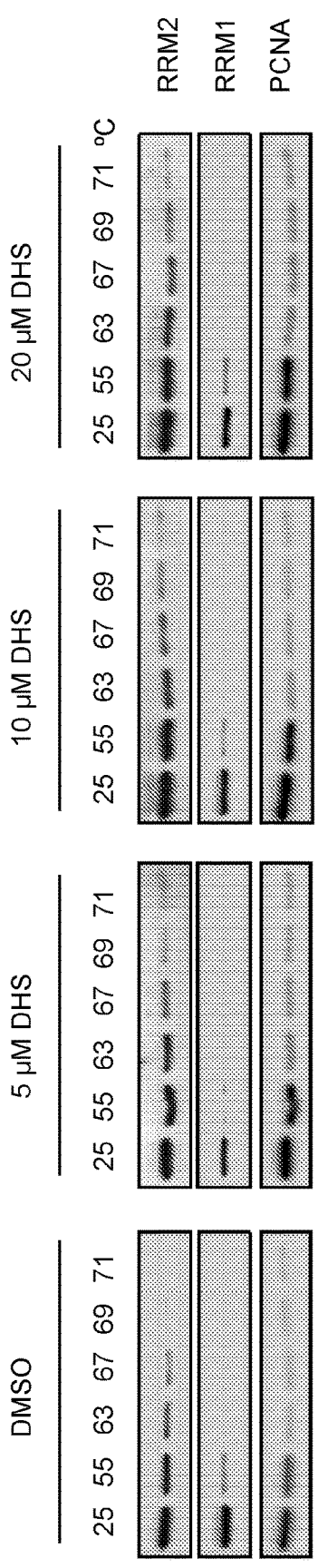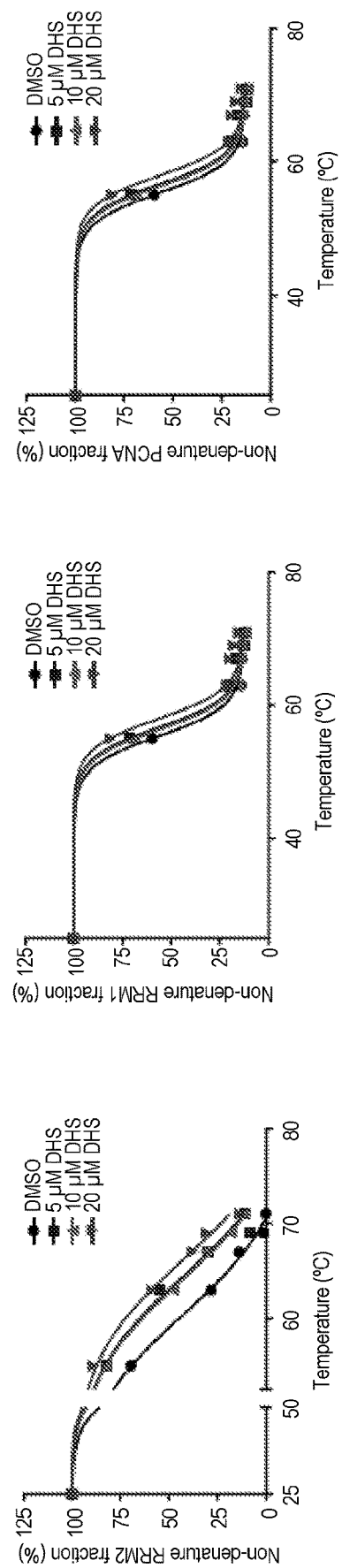
FIG. 11A
FIG. 11B
FIG. 11C
FIG. 11D

4,4'-TRANS-DIHYDROXYSTILBENE FOR USE IN TREATING CANCER

STATEMENT REGARDING FEDERALLY SPONSORED RESEARCH

This invention was made with government support under grant number CA177898 awarded by the National Institutes of Health. The government has certain rights in the invention.

BACKGROUND OF THE INVENTION

Certain cancer drugs, such as alkylating agents, platinum analogs, and cytidine analogs, target DNA and cause DNA damage. These drugs are thus cytotoxic. Nevertheless, these drugs have been widely used in either first-line therapy or adjuvant therapy for a variety of cancers. These agents can cause DNA damage, for example, by blocking DNA replication and transcription, and ultimately causing cell cycle arrest, premature senescence, or apoptosis. For example, certain anti-cancer agents block DNA replication and cause collapse of DNA replication forks, which then result in cell death (Roos et al., 2016). Currently, various drugs targeting DNA replication are being developed. ATR inhibitors, AZD6738 and VX-970, are being tested as monotherapeutic agents or in combination with other drugs in phase I/II trials against various cancer types. Inhibitors of ATM (AZD0156), CHK-1 (GDC-0575, MK-8776, and LY2606368), and WEE1 (AZD1775), which showed promising therapeutic effects in preclinical studies, are also being evaluated in phase I/II clinical studies (O'Connor, 2015).

Acidic nucleoplasmic DNA-binding protein 1 (And-1, also known as WDHD1) is a DNA replication fork-associated scaffold protein. It associates with DNA polymerases and helicases and regulates numerous DNA replication factors, including MCM Proteins (Li et al., 2012b). It also regulates histone acetyltransferase Gcn5 (Li et al., 2012a) and controls chromosome congression via regulating centromere protein A (CENP-A) (Jaramillo-Lambert et al., 2013). And-1 is normally under-expressed in normal cells but highly expressed in cancer cells, and furthermore, high levels of And-1 expression in lung cancers are correlated with poor prognosis and low survival rate (Sato et al., 2010). A study that used chromosome instability cancer gene orthologs in yeast to identify candidate targets for synthetic lethal killing of cancer cells with defined somatic mutations found that the yeast And-1 ortholog, Ctf4, is a hub gene (van Pel et al., 2013), suggesting that And-1 is a potentially important target for the development of anti-cancer agents.

Ribonucleotide reductase (RNR) is essential for DNA synthesis and repair based on its enzyme activity of converting ribonucleotides into 2'-deoxyribonucleotides. RNR is composed of a large homodimeric subunit, ribonucleotide reductase catalytic subunit M1 (RRM1), and a smaller homodimeric subunit, ribonucleotide reductase catalytic subunit M2 (RRM2) (Kohnken et al., 2015). The RRM1 subunit contains the catalytic site, the substrate-specificity site, and the activity site, while the RRM2 subunit is responsible for generating tyrosyl free radical necessary for enzymatic activity. Alternatively, a p53R2 protein can replace RRM2 to form an active RNR with RRM1 (Guittet et al., 2001). Three RNR inhibitors, hydroxyurea, 3-aminopyridine-2-carboxaldehyde thiosemicarbazone (3-AP, Triapine), and GTI2040, are used clinically. Inhibition of RNR can cause DNA strand breaks and loss of cell viability (Cory et al., 1983). The RNR inhibitor, COH29, inhibits cancer cell growth and overcomes gemcitabine resistance by targeting RRM2 (Zhou et al., 2013).

Resveratrol (3,5,4'-trihydroxy-trans-stilbene) belongs to a group of compounds known as stilbenes, and is a secondary metabolite produced by plants in response to stressful conditions, such as fungal infection or UV radiation (Hosseini et al., 2015). Resveratrol is reported to have antioxidant and DNA repair activities (Pangeni et al., 2014). Ongoing clinical trials are investigating use of resveratrol to treat colon cancer, liver cancer, neuroendocrine tumor, multiple myeloma, and prostate cancer (Varoni et al., 2016).

Drug resistance is an obstacle that jeopardizes the efficacy of chemotherapy and reduces the overall survival rate of cancer patients. During chemotherapy, cancer cells can develop resistance to chemotherapeutic agents by adjusting their pathological signaling and gene regulatory mechanisms. Recently, cancer genome sequencing has emerged as a powerful approach to identify pathways contributing to drug resistance. However, this approach has its own limitations. For instance, it is difficult to identify target pathway(s) from sequencing data, and some unique regulatory pathways, due to post-transcriptional modification, cannot be identified by genomic sequencing.

There is a need for therapeutic agents, e.g., small molecule drugs, that inhibit DNA replication and repair and that overcome drug resistance.

BRIEF SUMMARY OF THE INVENTION

The present disclosure is directed to a pharmaceutical composition comprising 4,4'-Trans-dihydroxystilbene (DHS) and a DNA damaging agent.

In certain embodiments, the DNA damaging agent is selected from the group consisting of a: chemotherapeutic agent, DNA alkylating agent, nucleoside analog, replication inhibitor, platinum-based drug, actinomycin, amsacrine, cyclophosphamide, dactinomycin, daunorubicin, doxorubicin, epirubicin, iphosphamide, merchlorehtamine, mitomycin, mitoxantrone, nitrosourea, procarbazine, taxol, taxotere, teniposide, etoposide, triethylenethiophosphoramide, hydroxyurea, gemcitabine, and any combination thereof.

In certain embodiments, the DNA damaging agent is gemcitabine.

In certain embodiments, the DNA damaging agent is hydroxyurea.

In certain embodiments, the DNA damaging agent is a platinum-based drug. In certain embodiments, the platinum-based drug is selected from the group consisting of: cisplatin, carboplatin, diplatinum cytostatic, iproplatin, oxaliplatin, nedaplatin, satraplatin, tetraplatin, and any combination thereof.

The present disclosure is directed to a kit comprising any of the above pharmaceutical compositions.

The present disclosure is directed to a method of treating cancer in a subject, comprising administering to the subject an effective dose of DHS.

The present disclosure is directed to a method of treating a disease or disorder in a subject characterized by overexpression of ribonucleotide reductase (RNR) or a subunit thereof, acidic nucleoplasmic DNA-binding protein 1 (And-1), or any combination thereof, comprising administering to the subject an effective dose of DHS. In certain embodiments, the RNR subunit is ribonucleotide reductase catalytic subunit M1 (RRM1). In certain embodiments, the RNR subunit is ribonucleotide reductase catalytic subunit M2 (RRM2).

In certain embodiments, any of the above methods further comprise administering to the subject an effective dose of a DNA damaging agent.

The present disclosure is directed to a method of decreasing resistance to a DNA damaging agent that is used in the treatment of a disease or disorder in a subject, comprising administering to the subject: a) an effective dose of DHS; and b) an effective dose of a DNA damaging agent.

In certain embodiments, the DNA damaging agent in any of the above methods is administered prior to, concurrently with, or subsequent to DHS.

In certain embodiments, the DNA damaging agent in any of the above methods is selected from the group consisting of a: chemotherapeutic agent, DNA alkylating agent, nucleoside analog, replication inhibitor, platinum-based drug, actinomycin, amsacrine, cyclophosphamide, dactinomycin, daunorubicin, doxorubicin, epirubicin, iphosphamide, merchlorehtamine, mitomycin, mitoxantrone, nitrosourea, procarbazine, taxol, taxotere, teniposide, etoposide, triethylenethiophosphoramide, hydroxyurea, gemcitabine, and any combination thereof.

In certain embodiments, the DNA damaging agent in any of the above methods is gemcitabine.

In certain embodiments, the DNA damaging agent in any of the above methods is hydroxyurea.

In certain embodiments, the DNA damaging agent in any of the above methods is a platinum-based drug. In certain embodiments, the platinum-based drug is selected from the group consisting of: cisplatin, carboplatin, diplatinum cytostatic, iproplatin, oxaliplatin, nedaplatin, satraplatin, tetraplatin, and any combination thereof.

In certain embodiments, the disease or disorder in any of the above methods is a cancer.

In certain embodiments, prior to initiation of any of the above methods the subject has been identified as having a cancer that is resistant to treatment with at least one DNA damaging agent.

In certain embodiments, the cancer in any of the above methods is selected from the group consisting of: ovarian cancer, testicular cancer, bladder cancer, head and neck cancer, oral cancer, esophageal cancer, lung cancer, small cell lung cancer, non-small cell lung cancer, breast cancer, cervical cancer, stomach cancer, gastric cancer, colorectal cancer, osteosarcoma, pancreatic cancer, prostate cancer, and any combination thereof.

Figure 1A:
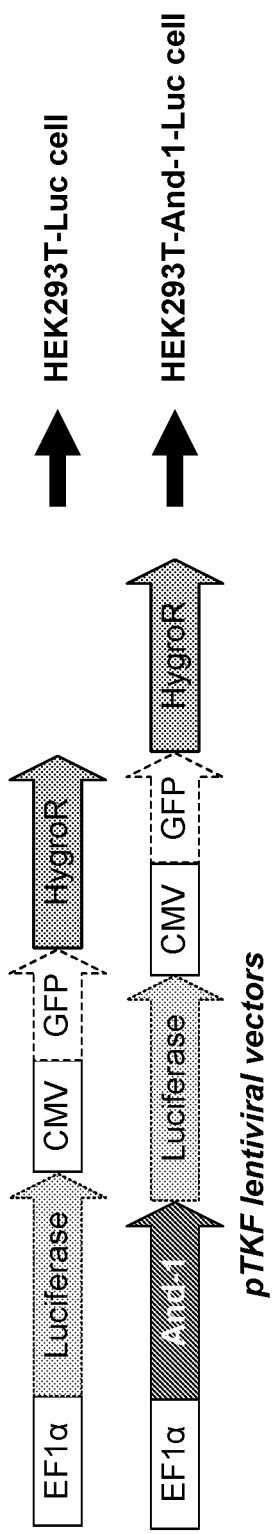
FIG. 1 shows identification of resveratrol (3,5,4'-trihydroxy-trans-stilbene) as an inducer of And-1 protein down-regulation. (A) HEK293T cells were infected with either a control lentiviral vector (pTKF) containing luciferase or a pTKF lentiviral vector containing And-1 and luciferase. EF1α=elongation factor 1 alpha promoter; CMV=cytomegalovirus promoter; GFP=green fluorescent protein; HygroR=hygromycin resistance gene. (B) Resveratrol was selected from a compound pool based on luciferase activity in infected 293T cells.

and actin (control) following treatment of HCT116 (wild-type (WT)) and HCT116-DHS-R (resistant) cells with DHS. (E) Western blot showing levels of And-1 and proliferating cell nuclear antigen (PCNA; control) protein in HCT116 cells in a thermal shift assay following treatment with DMSO or DHS. (F) Western blot following immunoprecipitation (IP) using either a control antibody (IP: IgG) or with an antibody against RRM1 (IP: RRM1) and immunoblotting (IB) using antibodies against RRM1 (IB: RRM1), RRM2 (IB: RRM2), and And-1 (IB: And-1).

FIG. 10 shows that DHS protects RRM2 in a thermal shift assay. (A) Western blot showing levels of RRM2, RRM1, and PCNA (control) proteins in HCT116 cells in a thermal shift assay after treatment with DMSO, DHS, resveratrol, gemcitabine, and hydroxyurea (Hu). (B)-(D) Graphs showing levels of non-denatured RRM2, RRM1, and PCNA protein in HCT116 cells, respectively, following the treatments in the thermal shift assay.

FIG. 11 shows that DHS protects RRM2 in a dose-dependent manner in a thermal shift assay. (A) Western blot showing levels of RRM2, RRM1, and PCNA (control) proteins in HCT116 cells in a thermal shift assay after treatment with DMSO or increasing amounts of DHS. (B)-(D) Graphs showing levels of non-denatured RRM2, RRM1, and PCNA protein in HCT116 cells, respectively, following the treatments in the thermal shift assay.

FIG. 12 shows that DHS binds RRM2. (A) Western blot showing non-denatured fraction levels of RRM2 and bovine serum albumin (control) purified proteins in a thermal shift assay after treatment with DMSO, DHS, or hydroxyurea (Hu). (B)-(C) Graphs showing levels of non-denatured RRM2 and BSA purified protein, respectively, following the treatments in the thermal shift assay of (A). (D) Western blot showing non-denatured fraction levels of truncated RRM2 protein lacking amino acid residues from glutamine 147 to isoleucine 166 of wild-type RRM2 (Flag-truncated RRM2) and PCNA (control) protein in HCT116 cells in a thermal shift assay after treatment with DMSO or DHS. (E) Western blot showing non-denatured fraction levels of RRM2 and PCNA (control) proteins in HCT116 cells in a thermal shift assay after treatment with DMSO, DHS, hydroxyurea (Hu), or a combination of DHS and Hu (DHS+Hu). (F)-(G) Graphs showing levels of non-denatured RRM2 and PCNA protein in HCT116 cells, respectively, following the treatments in the thermal shift assay of (E).

FIG. 13 shows that DHS causes DNA replication proteins to dissociate from DNA chromatin. (A) Western blot showing levels of And-1, RRM1, RRM2, Polymerase α (polα), and minichromosome maintenance complex component 7 (MCMI) proteins in whole cell, chromatin fraction, and soluble fraction from HCT116 cells treated with DHS. Actin and origin recognition complex subunit 2 (ORC2) proteins are controls. (B) Electrophoresis gel showing results of Topisomerase II decatenation assay. "Marker"=DNA ladder; "K-DNA"=kinetoplast DNA; "Negative control" is K-DNA without nuclear extracts; Positive control is K-DNA incubated with nuclear extracts. Incubation of DHS with kDNA also resulted in reduced bonds of decatenate K-DNA, demonstrating that DHS inhibits topoisomerase II activity via direct interactions with DNA.

FIG. 14 shows that DHS represses RRM1 protein through a proteasome degradation pathway. (A) Western blot showing levels of RRM2, RRM1, and GAPDH (control) proteins following treatment with or without the proteasome inhibitor MG132 prior to DHS treatment in HCT116 cells. (B) Western blot showing levels of RRM2, RRM1, and Actin (control) proteins following treatment with siRNAs directed against firefly luciferase encoded by the pGL2 reporter plasmid (siGL2, control), RRM1 (siRRM1), or RRM2 (siRRM2). (C) Western blot showing results of an ubiquitination assay. "FLAG-RRM2"=RRM2 protein tagged with a "FLAG" peptide, N-Asp-Tyr-Lys-Asp-Asp-Asp-Asp-Lys-C; "HA-Ubiquitin"=ubiquitin tagged with a "HA" peptide, YPYDVPDYA; "IP: FLAG"=immunoprecipitation (IP) using an antibody directed against the FLAG tag; and immunoblotting (IB) using antibodies against ubiquitin (IB: Ubiquitin), RRM2 (IB: RRM2), and the FLAG peptide (IB: FLAG) following treatment with or without the proteasome inhibitor MG132 prior to DHS treatment in HCT116 cells. (D) Western blot showing levels of RRM2, RRM1, Cyclin F, and Actin (control) proteins after treatment with siRNAs directed against siGL2 (control, as described for (B)) or Cyclin F (siCyclin F) prior to treatment with DMSO or DHS. (E) Graph showing percentage of viable cells following treatments in (D) as well as treatment with a siRNA directed against RRM2 (siRRM2) prior to DHS treatment.

FIG. 15 shows that DHS overcomes gemcitabine and hydroxyurea resistance by downregulating RRM2. (A-C) Graphs showing percentage of cell survival of an oral cancer cell line, "KB," and its gemcitabine-resistant and hydroxyurea-resistant sublines, "KB-Gem" and "KB-Hu," respectively, after treatment with gemcitabine (A), hydroxyurea (B), or DHS (C). (D) Western blot showing levels of RRM2, RRM1, and Actin proteins in KB, KB-Hu, and KB-Gem cells.

FIG. 16 shows that DHS acts synergistically with hydroxyurea (Hu) and gemcitabine. "KB," KB-Gem," and "KB-Hu" cell lines are as described for FIG. 15. (A) Graph showing percentage of relative cell viability following treatment with gemcitabine ("treated Gem") or gemcitabine and 10 μM DHS ("treated Gem+DHS (10 μM)"). (B) Graph showing treatment of cells with hydroxyurea ("treated Hu") or hydroxyurea and 10 μM DHS ("treated Hu+DHS (10 μM)"). (C-D) Graphs showing Loewe synergy and antagonism plots of combinatorial indexes following treatments with DHS and Hu (C) and DHS and gemcitabine (D).

FIG. 17 shows that RRM2/RRM1 levels are positively correlated with the DHS cytotoxicity. (A-B) Graphs showing percentage of surviving pancreatic cancer patients over time with low and high level of RRM2 (A) and RRM1 (B). (C) Western blot showing levels of RRM2, RRM1, and Actin proteins in various mouse-derived pancreatic tumor cells, PA4522, PA3124, PA3381, PA2016, PA4355, BP429, BP668, PA3608, PA3690, and PA1468. (D-E) Graphs showing relative DHS sensitivity in terms of cell viability after treatment with DHS in association with expression levels of RRM2 (D) and RRM1(E).

FIG. 18 shows that DHS acts synergistically with gemcitabine. (A) Graph showing percentage of relative cell viability following treatment of a human pancreatic cancer line, "PK-9," and it gemcitabine-resistant subline, "RPK-9," with either gemcitabine or 10 μM DHS and gemcitabine ("10 μM DHS+Gem"). (B) Graph showing Loewe synergy and antagonism plots of combinatorial indexes following treatment with DHS and gemcitabine. (C) Western blot showing expression of RRM2, RRM1, and Actin (control) proteins following treatment with or without DHS, gemcitabine, or both. (D) Graph showing apoptosis as shown by propidium iodide (PI) and Annexin V staining after treatment with DMSO, DHS, gemcitabine, or DHS and gemcitabine. Percentages at the bottom of each square refer to early apoptotic cells, while percentages at the top of each square refer to late apoptotic cells.

Figure 18A:
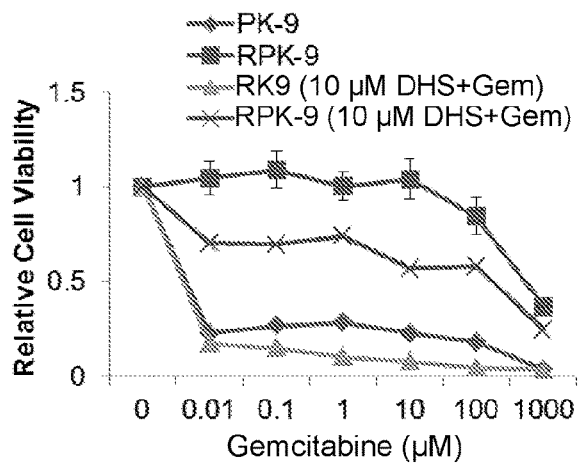
Figure 18B:
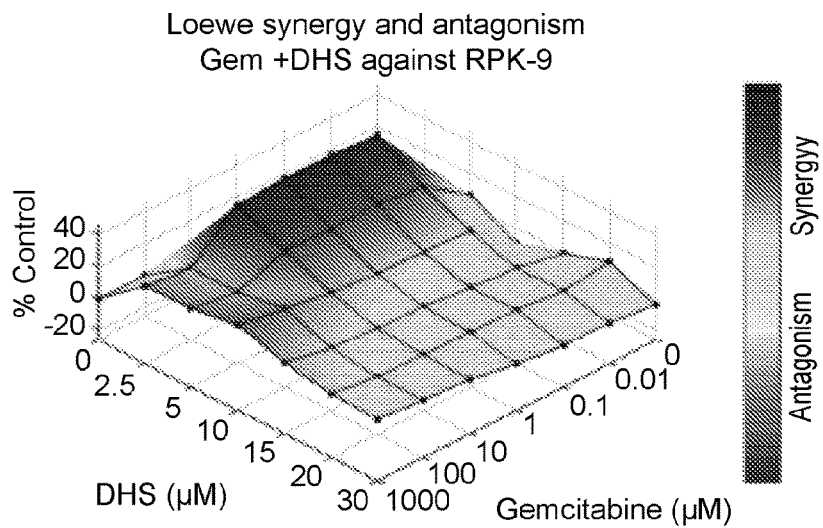
Figure 18C:
Figure 18D:
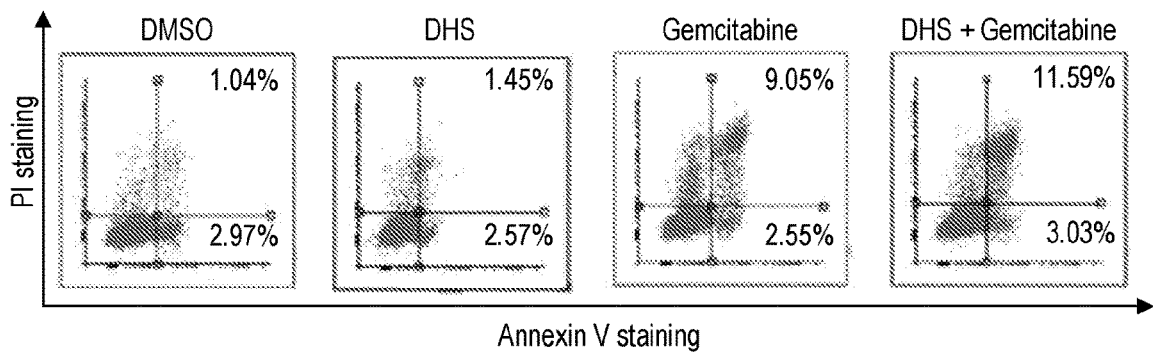
Figure 19A:
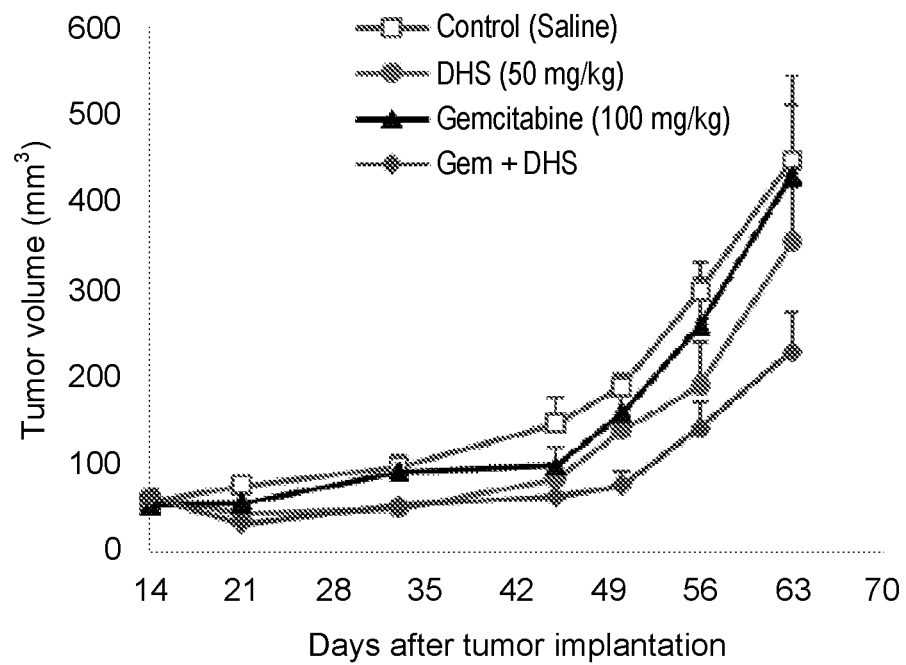
Figure 19B:
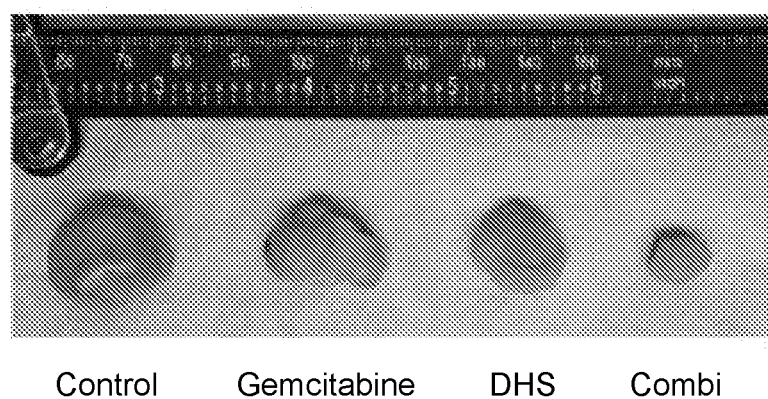

FIG. 19 shows that DHS alone and in combination with gemcitabine reduces growth of tumors in vivo. (A) Graph showing effect of saline (Control), DHS, gemcitabine, and the combination of gemcitabine and DHS ("Gem+DHS") on tumor volume in a RPK-9 xenograft tumor model, with RPK-9 as described for FIG. 18. (B) Photograph of tumors showing sizes after the treatments in (A). "Combi" refers to treatment with DHS and gemcitabine.

FIG. 20 shows that DHS alone and in combination with cisplatin reduces growth of tumors in vivo. (A) Graph showing effect of vehicle (saline control), DHS, cisplatin, and the combination of DHS and cisplatin ("Combo") on tumor volume in a xenograft tumor model using cisplatin-resistant human ovarian cancer cells (IGROV1 CR). (B) Photograph of tumors showing sizes after the treatments in (A). "Veh" refers to treatment with vehicle. (C) Graph showing effect of vehicle (saline control), DHS, cisplatin, and the combination of DHS and cisplatin on tumor volume in a xenograft tumor model using human colon carcinoma HCT116 cells. (D) Photograph of tumors showing sizes after the treatments in (C). "Control" refers to treatment with saline; "Combine" refers to treatment with DHS and cisplatin. $*=p<0.05$, $=p<0.01$, $*=p<0.001$ by two-way ANOVA.

FIG. 21 shows lack of toxicity associated with DHS treatment. (A) Graph showing percentage of body weight over time in a xenograft tumor model using HCT116 cells as compared to initial weight following treatment with vehicle (saline control), DHS, cisplatin, and the combination of DHS and cisplatin. (B) Photographs of histologically stained sections of tissues following the treatments of (A).

Figure 22:
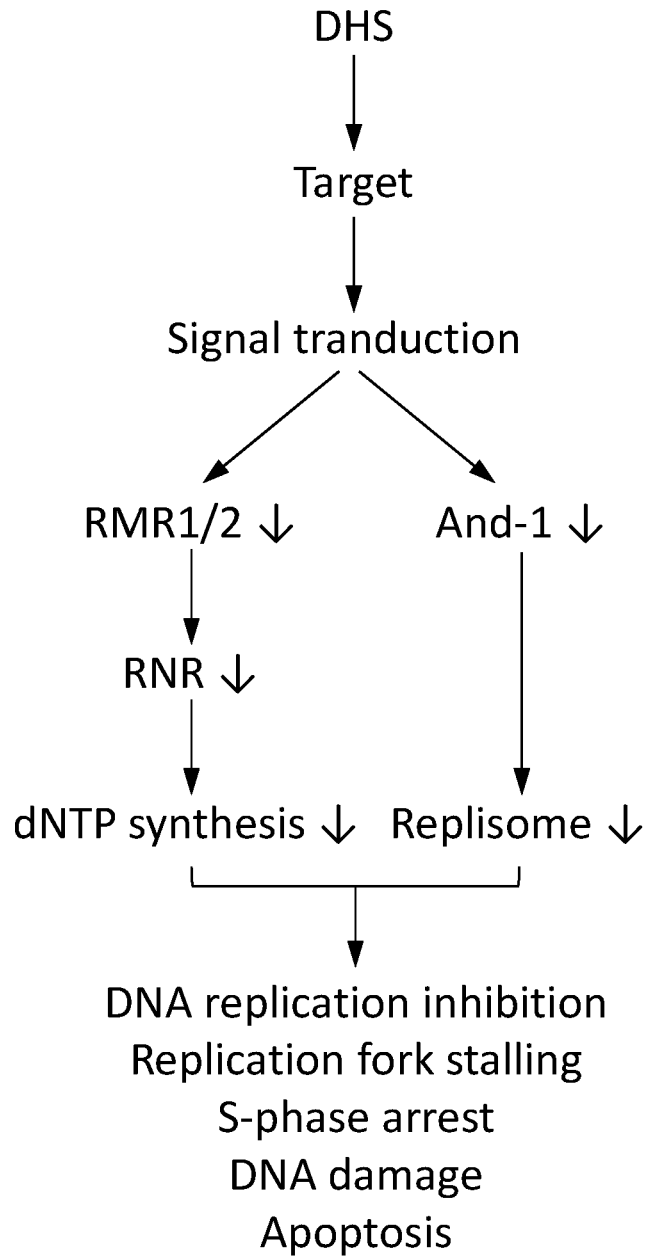

FIG. 22 shows a flowchart depicting the mechanism of action and effects associated with DHS treatment.

DETAILED DESCRIPTION OF THE INVENTION

The present disclosure provides methods, pharmaceutical compositions, dosing regimens, and kits comprising 4,4'-trans-dihydroxystilbene (DHS), including methods of treating cancer in a subject and methods of decreasing or reversing resistance to a DNA damaging agent in a subject.

The headings provided herein are not limitations of the various aspects or aspects of the disclosure, which can be defined by reference to the specification as a whole. Accordingly, the terms defined immediately below are more fully defined by reference to the specification in its entirety. Before describing the present disclosure in detail, it is to be understood that this invention is not limited to specific compositions or process steps, as such can vary.

I. Terminology

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular.

As used herein and in the appended claims, the singular forms "a," "an," and "the" include plural references unless the context clearly dictates otherwise. For example, the term "a DNA damaging agent" or "at least one DNA damaging agent" can include a plurality of DNA damaging agents, including mixtures thereof. The terms "a", "an," "the," "one or more," and "at least one," for example, can be used interchangeably herein.

As used herein, the term "about," when used to modify an amount related to the invention, refers to variation in the numerical quantity that can occur, for example, through routine testing and handling; through inadvertent error in such testing and handling; through differences in the manufacture, source, or purity of ingredients employed in the invention; and the like. Whether or not modified by the term "about," the claims include equivalents of the recited quantities. In some embodiments, the term "about" means plus or minus 10% of the reported numerical value.

Throughout this application, various embodiments of this invention can be presented in a range format. It should be understood that the description in range format is merely for convenience and brevity and should not be construed as an inflexible limitation on the scope of the invention. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Accordingly, the description of a range should be considered to have specifically disclosed all the possible subranges as well as individual numerical values within that range. For example, description of a range, such as from 1 to 6 should be considered to have specifically disclosed subranges such as from 1 to 2, from 1 to 3, from 1 to 4, from 1 to 5, from 2 to 3, from 2 to 4, from 2 to 5, from 2 to 6, from 3 to 4, from 3 to 5, from 3 to 6, etc., as well as individual numbers within that range, for example, 1, 2, 3, 4, 5, and 6, and subranges of less than whole number such as 1.1, 1.2, 1.3, 1.4, etc. This applies regardless of the breadth of the range.

The terms "comprises," "comprising," "includes," "including," "having," and their conjugates are interchangeable and mean "including but not limited to." It is understood that wherever aspects are described herein with the language "comprising," otherwise analogous aspects described in terms of "consisting of" and/or "consisting essentially of" are also provided.

The term "consisting of" means "including and limited to."

The term "consisting essentially of" means the specified material of a composition, or the specified steps of a method, and those additional materials or steps that do not materially affect the basic characteristics of the material or method.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

As used herein, the term "effective dose" of an agent is that amount sufficient to effect beneficial or desired results, for example, clinical results, and, as such, an "effective dose" depends upon the context in which it is being applied. The term "effective dose" can be used interchangeably with "effective amount," "therapeutically effective amount,"

"therapeutically effective dose," "clinically effective amount," or "clinically effective dose."

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Administration of any one agent as described herein "in combination with" one or more other agents includes simultaneous (concurrent) and consecutive administration in any order. By "combination" or "in combination with," it is not intended to imply that the therapy or the therapeutic agents must be administered at the same time and/or formulated for delivery together (e.g., in the same composition), although these methods of delivery are within the scope described herein.

The terms "invention" and "disclosure" can be used interchangeably when describing or used, for example, in the phrases "the present invention" or "the present disclosure."

As used herein, the terms "chemotherapeutic agent" and "chemotherapeutic drug" are interchangeable and refer to a chemical compound useful in the treatment of cancer, regardless of mechanism of action.

As used herein, the term "excipient" refers to a component, or mixture of components, that is used to give desirable characteristics to a pharmaceutical composition or dosage form as disclosed herein. An excipient of the present invention can be described as a "pharmaceutically acceptable" excipient, meaning that the excipient is a compound, material, composition, salt, and/or dosage form which is, within the scope of sound medical judgment, suitable for contact with tissues of animals (i.e., humans and non-human animals) without excessive toxicity, irritation, allergic response, or other problematic complications over the desired duration of contact commensurate with a reasonable benefit/risk ratio.

As used herein, the term "expression" when used in relation to a nucleic acid refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

As used herein, the term "pharmaceutical composition" refers to a preparation which is in such form as to permit the biological activity of the active ingredient to be effective, and which contains no additional components which are unacceptably toxic to a subject to which the composition would be administered. Such composition can be sterile.

As used herein, the term "subject" or "individual" or "animal" or "patient" or "mammal," means any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears; food animals such as cows, pigs, and sheep; ungulates such as deer and giraffes; rodents such as mice, rats, hamsters and guinea pigs; and so on. In certain embodiments, the mammal is a human subject. In other embodiments, a subject is a human patient. In certain embodiments, a subject is a human patient in need of a cancer treatment. In certain embodiments, a subject is a human male and/or a human female. The term "cancer patient" as used herein is meant to include any subject being treated for cancer, including, but not limited to, humans and veterinary animals.

As used herein, the term "treating" or "treatment" or "therapy" refers to partially or completely alleviating, ameliorating, improving, relieving, delaying onset of, inhibiting progression of, reducing severity of, and/or reducing incidence of one or more symptoms or features of disease or disorder, including a condition, (e.g., a cancer). For example, "treating" a cancer can refer to inhibiting growth and/or spread of a cancer. Treatment can be administered to a subject who does not exhibit signs of a disease or disorder and/or to a subject who exhibits only early signs of a disease or disorder for the purpose of decreasing the risk of developing pathology associated with the disease or disorder.

It is appreciated that certain features of the invention, which are, for clarity, described in the context of separate embodiments, can also be provided in combination in a single embodiment. Conversely, various features of the invention, which are, for brevity, described in the context of a single embodiment, can also be provided separately or in any suitable subcombination or as suitable in any other described embodiment of the invention. Certain features described in the context of various embodiments are not to be considered essential features of those embodiments, unless the embodiment is inoperative without those elements.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

II. Pharmaceutical Compositions and Kits

In one aspect, the present invention is directed to a pharmaceutical composition comprising 4'-trans-dihydroxystilbene (DHS) and a DNA damaging agent.

In another aspect, the present invention is directed to a dosing regimen comprising DHS and a DNA damaging agent. In some embodiments, the dosing regimen comprises a dosage form comprising DHS and the DNA damaging agent. In some embodiments, the dosing regimen comprises a first dosage form comprising DHS and a second dosage form comprising the DNA damaging agent. In some embodiments, the first dosage form is for administration prior to, concurrently with, or subsequent to the second dosage form.

In some embodiments, a pharmaceutical composition or dosage regimen as disclosed herein is for use in: treating cancer; treating a disease or disorder in a subject characterized by overexpression of ribonucleoside reductase (RNR) or a subunit thereof, acidic nucleoplasmic DNA-binding protein 1 (And-1), or any combination thereof; decreasing resistance to a DNA damaging agent that is used in the treatment of a disease or disorder in a subject; preventing or delaying development of resistance or tolerance in a subject or reducing or eliminating an existing resistance or tolerance in a subject; inhibiting DNA replication; inhibiting And-1, RRM1, and/or RRM2; binding RRM2; mediating protein degradation by the Cyclin F pathway; causing cell cycle arrest at S-phase; causing DNA replication fork stalling; causing dNTP depletion; causing DNA damage; or any combination thereof.

In some embodiments, a pharmaceutical composition or a dosing regimen as disclosed herein is for use in treating cancer.

In some embodiments, a pharmaceutical composition or a dosing regimen as disclosed herein is for treating a disease or disorder in a subject characterized by overexpression of ribonucleoside reductase (RNR) or a subunit thereof, acidic nucleoplasmic DNA-binding protein 1 (And-1), or any combination thereof. In some embodiments, the RNR subunit is ribonucleotide reductase catalytic subunit M1 (RRM1). In some embodiments, the RNR subunit is ribonucleotide reductase catalytic subunit M2 (RRM2). In some embodiments, the RNR subunit is both RRM1 and RRM2. In some embodiments, the disease or disorder is a cancer.

In some embodiments, a pharmaceutical composition or a dosing regimen as disclosed herein is for decreasing resistance to a DNA damaging agent that is used in the treatment of a disease or disorder in a subject. The term "resistance to a DNA damaging agent" can be used interchangeably with the term "tolerance to a DNA damaging agent" and refers to a diminishing therapeutic benefit of a DNA damaging agent in treating a disease or disorder in a subject over time. "Decreasing" resistance or tolerance as referred to herein can include any decrease in resistance or tolerance that provides a therapeutic benefit, including preventing or delaying development of resistance or tolerance in a subject or reducing or eliminating an existing resistance or tolerance in a subject. In some embodiments, a pharmaceutical composition or a dosing regimen as disclosed herein is for preventing or delaying development of resistance or tolerance to a DNA damaging agent in a subject. In some embodiments, a pharmaceutical composition or a dosing regimen as disclosed herein is for reducing or eliminating an existing resistance or tolerance to a DNA damaging agent in a subject. In some embodiments, a pharmaceutical composition or a dosing regimen as disclosed herein is for treating a disease or disorder in a subject with existing resistance or tolerance to a DNA damaging agent. In some embodiments, the disease or disorder is a cancer.

In some embodiments, the cancer is selected from the group consisting of: ovarian cancer, testicular cancer, bladder cancer, head and neck cancer, oral cancer, esophageal cancer, lung cancer, small cell lung cancer, non-small cell lung cancer, breast cancer, cervical cancer, stomach cancer, gastric cancer, colorectal cancer, osteosarcoma, pancreatic cancer, prostate cancer, and any combination thereof. In some embodiments, the cancer is oral cancer. In some embodiments, the cancer is pancreatic cancer. In some embodiments, the cancer is ovarian cancer. In some embodiments, the cancer is colorectal cancer.

A "DNA damaging agent" can be any therapeutic agent that causes DNA damage, including, but not limited to: chemotherapeutic agents, DNA alkylating agents, nucleoside analogs, replication inhibitors, platinum-based drugs, actinomycin, amsacrine, cyclophosphamide (Cytoxan®), dactinomycin, daunorubicin, doxorubicin, epirubicin, iphosphamide, merchlorehtamine, mitomycin, mitoxantrone, nitrosourea, procarbazine, taxol, taxotere, teniposide, etoposide, triethylenethiophosphoramide, hydroxyurea, gemcitabine, or any combination thereof. In some embodiments, the DNA damaging agent is gemcitabine. In some embodiments, the DNA damaging agent is hydroxyurea.

In some embodiments, the DNA damaging agent is a DNA alkylating agent, including, but not limited to: mechlorethamine, uramustine, streptozocin, busulfan, Shionogi 254-S, aldo-phosphamide analogues, altretamine, anaxirone, Boehringer Mannheim BBR-2207, bendamustine, bestrabucil, budotitane, Wakunaga CA-102, carmustine, Chinoin-139, Chinoin-153, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, melphalan, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromustine, Tanabe Seiyaku TA-077, tauromustine, temozolomide, teroxirone, tetraplatin, trimelamol, or any combination thereof.

In some embodiments, the DNA damaging agent is a platinum-based drug, including a platinum analog or platinum. The terms "platinum-based drug" and "platinum-based chemotherapeutic drug" can be used interchangeably herein. In some embodiments, the platinum-based drug includes, but is not limited to, cisplatin, carboplatin, diplatinum cytostatic, iproplatin, oxaliplatin, nedaplatin, satraplatin, tetraplatin, or any combination thereof.

In some embodiments, a pharmaceutical composition or dosage form as described herein further comprise a pharmaceutically acceptable excipient (e.g., a diluent, carrier, salt or adjuvant). See, e.g., Remington, The Science and Practice of Pharmacy 20th Edition Mack Publishing, 2000. Suitable pharmaceutically acceptable vehicles and/or excipients include, but are not limited to, nontoxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN or polyethylene glycol (PEG).

In some embodiments, a pharmaceutical composition or dosage form as disclosed herein further comprises an additional therapeutic agent (e.g., a compound having anti-cancer properties).

In some embodiments, the additional therapeutic agent is a small molecule, an antibody, or an oligonucleotide.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, Fv, Fsc, CDR regions, or any portion of an antibody that is capable of binding an antigen or epitope), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. The modifier "monoclonal" indicates the character of the antibody as being obtained from a substantially homogeneous population of antibodies, and is not to be construed as requiring production of the antibody by any particular method. The term "antibody" as used herein also includes single-domain antibodies (sdAb) and fragments thereof that have a single monomeric variable antibody domain (VH) of a heavy-chain antibody. sdAb, which lack variable light (VL) and constant light (CL) chain domains are natively found in camelids (VHH) and cartilaginous fish (VNAR) and are sometimes referred to as "Nanobodies" by the pharmaceutical company Ablynx who originally developed specific antigen binding sdAb in llamas. An antibody can be of any of the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc. (e.g., immunoconjugates).

In some embodiments, the antibody is a blocking antibody or antagonist antibody. A "blocking" antibody or an "antagonist" antibody is one which inhibits or reduces biological activity of the antigen it binds. In some embodiments, blocking antibodies or antagonist antibodies substantially or completely inhibit the biological activity of the antigen. The biological activity can be reduced, for example, by about 10%, about 20%, about 30%, about 40%, about 50%, about 60%, about 70%, about 80%, about 90%, about 95%, or about 100%.

In some embodiments, the antibody is an "antibody fragment," which refers to an antigen-binding portion of an intact antibody. Examples of antibody fragments include, but are not limited to Fab, Fab', F(ab')2, and Fv fragments, linear antibodies, single chain antibodies, and multispecific antibodies formed from antibody fragments.

In some embodiments, the antibody specifically binds a target. By "specifically binds," it is generally meant that an antibody binds to an epitope of a target via the antibody's antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope.

An oligonucleotide inhibitor can include RNA and/or DNA, and modified forms thereof, capable of binding to a target nucleic acid and preventing expression of the target nucleic acid, including, but not limited to, antisense DNA/RNA, small interfering (siRNA), microRNA (miRNA), asymmetrical interfering RNA (aiRNA), Dicer-substrate RNA (dsRNA), and small hairpin RNA (shRNA).

Formulations of the pharmaceutical compositions and dosage forms as described herein can be prepared by any method known or developed in the art of pharmacology. In general, such preparatory methods include the step of bringing an active ingredient of the present invention (e.g., DHS, a DNA damaging agent, and/or an additional therapeutic agent) into association with an excipient and/or one or more other accessory ingredients, and then, if necessary and/or desirable, dividing, shaping and/or packaging the product into a desired single- or multi-dose unit.

Relative amounts of an active ingredient (e.g., DHS, or DNA damaging agent, and/or an additional therapeutic agent), the pharmaceutically acceptable excipient, and/or any additional ingredients in a pharmaceutical composition or dosage form in accordance with the present disclosure will vary, depending upon the identity, size, and/or condition of the subject treated and further depending upon the route by which the composition is to be administered. By way of example, the composition can comprise between about 0.1% and about 100%, e.g., between about 0.5 and about 50%, between about 1 to about 30%, between about 5 to about 80%, or at least about 80% (w/w) of an active ingredient.

The pharmaceutical compositions and dosage forms of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration.

In some embodiments, a pharmaceutical composition or dosage regimen as disclosed herein can provide "synergy" and prove "synergistic", i.e. the effect achieved when the active ingredients used together is greater than the sum of the effects that results from using the compounds separately. A synergistic effect can be attained when the active ingredients are: (1) co-formulated and administered or delivered simultaneously in a combined pharmaceutical composition or unit dosage form; (2) delivered by alternation or in parallel as separate pharmaceutical compositions or dosage forms; or (3) by some other regimen. When delivered in alternation therapy, a synergistic effect can be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

In one aspect, the present invention provides a kit comprising a pharmaceutical composition or dosing regimen as disclosed herein. In some embodiments, the kit comprises a first pharmaceutical composition or dosage form comprising DHS and a second pharmaceutical composition or dosage form comprising a DNA damaging agent as disclosed herein. In certain embodiments, a kit comprises DHS and at least one DNA damaging agent of the invention in one or more containers. In some embodiments, the kit comprises DHS and at least one DNA damaging agent in a single pharmaceutical composition or dosage form. In some embodiments, the kit comprises DHS and at least one DNA damaging agent as separate pharmaceutical compositions or dosage forms. In some embodiments, the kit comprises a pharmaceutical composition or dosage form comprising DHS and one or more DNA damaging agents. In some embodiments, the kit comprises separate pharmaceutical compositions or dosage forms for DHS and each one or more DNA damaging agents. It will further be appreciated that an additional therapeutic agent can be provided together in a single pharmaceutical composition or dosage form with DHS and/or the DNA damaging agent, or provided separately in different pharmaceutical compositions or dosage forms. In some embodiments, the kit comprises instructions for combined use of DHS and the DNA damaging agent. In some embodiments, a kit comprises DHS and a DNA damaging agent as described herein as separate compositions, and the kit further comprises instructions for making a pharmaceutical composition comprising both DHS and the DNA damaging agent. In some embodiments, a kit as described herein contains all of the components necessary and/or sufficient for administering DHS, the DNA damaging agent, and any additional therapy or therapeutic agent as disclosed herein. One skilled in the art will readily recognize that DHS and the DNA damaging agents of the present invention can be readily incorporated into one of the established kit formats which are well known in the art.

III. Methods

In one aspect, the present invention is directed to a method of treating cancer in a subject, comprising administering to the subject an effective dose of DHS. In some embodiments, the method further comprises administering an effective dose of a DNA damaging agent to the subject.

In another aspect, the present invention is directed to a method of treating a disease or disorder in a subject characterized by overexpression of ribonucleotide reductase (RNR) or a subunit thereof, acidic nucleoplasmic DNA-binding protein 1 (And-1), or any combination thereof, comprising administering to the subject an effective dose of DHS. In some embodiments, the RNR subunit is ribonucleotide reductase catalytic subunit M1 (RRM1). In some embodiments, the RNR subunit is ribonucleotide reductase catalytic subunit M2 (RRM2). In some embodiments, the RNR subunit is both RRM1 and RRM2. In some embodiments, the method further comprises administering an effective dose of a DNA damaging agent to the subject. In some embodiments, the disease or disorder is a cancer.

In another aspect, the present invention is directed to a method of decreasing resistance to a DNA damaging agent that is used in the treatment of a disease or disorder in a subject, comprising: a) administering to the subject an effective dose of DHS; and b) administering to the subject an effective dose of a DNA damaging agent. In some embodiments, the method is for preventing or delaying development of resistance or tolerance to a DNA damaging agent in a subject. In some embodiments, the method is for reducing or eliminating an existing resistance or tolerance to a DNA damaging agent in a subject. In some embodiments, the method is for treating a disease or disorder in a subject with existing resistance or tolerance to a DNA damaging agent. In some embodiments, the disease or disorder is a cancer.

In some embodiments, DHS in a method as disclosed herein: inhibits DNA replication; inhibits And-1, RRM1, and/or RRM2; binds RRM2; mediates protein degradation by the Cyclin F pathway; causes cell cycle arrest at S-phase; causes DNA replication fork stalling; causes dNTP depletion; causes DNA damage; and any combination thereof.

It is understood that methods of administering DHS as disclosed herein can alternatively be described as uses of DHS in the preparation of medicaments, or DHS for a disclosed use (e.g., for treating cancer; for treating a disease or disorder in a subject characterized by overexpression of RNR or a subunit thereof, And-1, or any combination thereof; or for decreasing resistance to a DNA damaging agent that is used in the treatment of a disease or disorder in a subject).

In the context of treating cancer, an effective dose is, for example, an amount sufficient to reduce or decrease a size of a tumor (i.e., reduce or decrease the size of a tumor mass), decrease the rate of or inhibit a tumor growth, decrease the number of metastases, result in amelioration of one or more symptoms of cancer, prevent advancement of cancer, cause regression of the cancer, increase time to tumor progression, increase tumor cell apoptosis, increase survival time (e.g., increase survival time by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%), or otherwise benefit a subject with cancer as compared to the response obtained without administration of the agent.

In some embodiments, prior to initiation of the method the subject has been identified as having a cancer that is resistant to treatment with at least one DNA damaging agent. In some embodiments, a method as disclosed herein further comprises determining whether the subject has a cancer that is resistant to treatment with the DNA damaging agent prior to administering the DNA damaging agent and the inhibitor.

In some embodiments, the cancer is selected from the group consisting of: ovarian cancer, testicular cancer, bladder cancer, head and neck cancer, oral cancer, esophageal cancer, lung cancer, small cell lung cancer, non-small cell lung cancer, breast cancer, cervical cancer, stomach cancer, gastric cancer, colorectal cancer, osteosarcoma, pancreatic cancer, prostate cancer, and any combination thereof. In some embodiments, the cancer is oral cancer. In some embodiments, the cancer is pancreatic cancer. In some embodiments, the cancer is ovarian cancer. In some embodiments, the cancer is colorectal cancer.

In some embodiments, the DNA damaging agent can be administered prior to, concurrently with, or subsequent to DHS.

In some embodiments, the DNA damaging agent is selected from the group consisting of a: chemotherapeutic agent, DNA alkylating agent, nucleoside analog, replication inhibitor, platinum-based drug, actinomycin, amsacrine, cyclophosphamide (Cytoxan®), dactinomycin, daunorubicin, doxorubicin, epirubicin, iphosphamide, merchlorethamine, mitomycin, mitoxantrone, nitrosourea, procarbazine, taxol, taxotere, teniposide, etoposide, triethylenethiophosphoramide, hydroxyurea, gemcitabine, or any combination thereof. In some embodiments, the DNA damaging agent is gemcitabine. In some embodiments, the DNA damaging agent is hydroxyurea. In some embodiments, the DNA damaging agent is a platinum-based drug. In some embodiments, the platinum-based drug is selected from the group consisting of: cisplatin, carboplatin, diplatinum cytostatic, iproplatin, oxaliplatin, nedaplatin, satraplatin, tetraplatin, and any combination thereof.

The DNA damaging agent of the methods can be any DNA damaging agent as described above with respect to the pharmaceutical compositions and dosing regimens of the invention.

In some embodiments, a method as disclosed herein comprises administering a pharmaceutical composition, a dosing regimen, or a dosage form as described herein.

In some embodiments, a method as disclosed herein further comprises administering one or more other additional therapies or therapeutic agents.

DHS, the DNA damaging agent, and any other additional therapeutic agent in a method as disclosed herein can be administered in any order. In general, each agent (i.e., DHS, each DNA damaging agent, and any other additional therapeutic agent) will be administered at a dose and/or on a time schedule determined for that agent. It will further be appreciated that an additional therapeutic agent can be administered together in a single pharmaceutical composition or dosage form with DHS and/or the DNA damaging agent, or administered separately in a different pharmaceutical composition or dosage form. In general, it is expected that an agent will be utilized at a level in the methods that does not exceed the level at which the agent is utilized individually. In some embodiments, the level of agent utilized in the methods will be lower than the level of the agent utilized individually.

DHS, the DNA damaging agent, and/or any additional therapeutic agent in a method as disclosed herein can be manufactured and/or formulated by the same or different manufacturers. DHS, the DNA damaging agent, and/or any additional therapeutic agent can thus be entirely separate pharmaceutical compositions or dosage forms. In some embodiments, instructions for their combined use are provided: (i) prior to release to physicians (e.g., in a "kit" comprising DHS, the DNA damaging agent, and any additional therapeutic agent); (ii) by the physicians themselves (or under the guidance of a physician) shortly before administration; or (iii) to the patient themselves by a physician or medical staff.

EXAMPLES

Reference is now made to the following examples, which together with the above descriptions illustrate some embodiments of the invention in a non-limiting fashion.

Materials and Methods

Chemicals and reagents. Resveratrol (3,5,4'-trihydroxy-trans-stilbene), DHS ((E)-4,4'-(ethane-1,2-diyl)diphenol), analog 1 (4,4'-((1E,3E)-buta-1,3-diene-1,4-diyl)diphenol), analog 2 (4,4'-((1E,3E,5E)-hexa-1,3,5-triene-1,6-dyl)diphenol), analog 3 ((E)-4-styrylphenol), analog 4((E)-4-styrylbenzene-1,2-diol), and analog 5 (4-((1E,3E)-4-phenylbuta-1,3-dien-1-yl)benzene-1,2-diol) (FIG. 1C) were reported before (Cai, 2004). Other chemicals and reagents were purchased by Sigma-Aldrich (St. Louis, Mo., US) except for those that are specifically specified. For all experiments, resveratrol and analogs stock solutions were freshly prepared in DMSO.

Cell lines and cell culture. HCT116, U2OS, PANC-1, MDA-231 cell lines were purchased from the American Type Culture Collection (Rockville, Md., US). Cells were cultured in the DMEM medium (Lonza, Basel, Switzerland) containing 10% fetal bovine serum (Gibco, Grand Island, N.Y., US), 100 Units/ml penicillin, 100 Units/mL streptomycin, 29.2 mg/mL L-glutamine (Gibco, Grand Island, N.Y., US) at 37° C. in a humidified atmosphere with 5% $CO_2$.

In vitro cytotoxicity assays. Cells growing in the Log phase were treated with various compounds at different concentrations (generally 0.137 to 100 µM) for 72 hours at 37° C. SRB assay (Vichai and Kirtikara, 2006) was performed and the absorbance at 510 nm was read with a plate reader. The proliferation rate was calculated according to the Manufacturer's instruction. The $IC_{50}$ value for each compound was determined from dose-effect relationship using the CompuSyn software (version 1.0.1; CompuSyn, Inc, Paramus, N.J.) (Chou, 2006). Cell proliferating doubling time was monitored over a period of 72 hours.

Xenograft mouse models. The guidelines of our institutional Animal Research Facility and the Animal Care and Use Committee were followed during animal experiments in this study. Six-week old female nude athymic mice were purchased from the Jackson Laboratory (ME, US). In xenograft studies, HCT116 ($3 \times 10^6$ cells) and IGROV3/CP2 ($5 \times 10^6$ cells) suspended in 100 µl of phosphate buffered saline (PBS, pH 7.4) were injected subcutaneously into the lower flank of the mice. Testing compounds were dissolved in DMSO/Tween 80/saline (10:10:80; v/v/v) buffer and were used to treat animals through intraperitoneal (i.p.) injection. DHS (50 mg/kg) were delivered for 14 consecutive days. Cisplatin (8 mg/kg) was given twice a week (Monday and Thursday). In combination treatment, animals received a DHS injection 15 min before cisplatin injection. The body weight of animals was measured throughout the study. Tumor diameters were measured with digital calipers, and the tumor volume in $mm^3$ was calculated by the formula: Volume=(width)$^2$×length/2.

Comet assay. HCT116 cells were treated with DHS for 0.5 or 24 hours. Afterward, the cells were irradiated with X-rays at a dose of 20 Gy. An aliquot of 80 µL cell suspension were mixed with 400 µL 1.2% low melting point agarose and plated on Fisherfinest microscope slide (Thermo Scientific, Pittsburgh, Pa., US), which had already been layered with 120 µL 1% agarose gel. Cells were then lysed and DNA was electrophoretically separated. The gels were neutralized before staining with 60 µL of 5 µM SYBR green. The shape of the stained DNA mass in at least 50 cells in each sample was analyzed with OpenComet software (MA, US).

Western blot analysis. Compound-treated cells were harvested and lysed. Protein extracts were subjected to electrophoresis in a SDS-polyacrylamide gel. The resolved proteins were transferred onto polyvinylidene difluoride membranes (Amersham Biosciences, Piscataway, N.J., US). After the blocking step, membranes were incubated with primary IgG antibodies, washed, and then incubated with horseradish peroxidase-conjugated anti-rabbit IgG or anti-mouse IgG secondary antibodies. Western blot signals were visualized by chemiluminescence using SuperSignal West Pico chemiluminescence reagent (Pierce, Rockford, Ill., US).

Example 1

Identification of DHS as an Inhibitor of And-1

And-1 plays a critical role in DNA replication and repair. A synthetic lethality analysis suggested that And-1 is a hub for anti-cancer drugs. Our review of clinical databases and literature indicated that patients with lung cancer, breast cancer, bladder urothelial carcinoma, pancreatic adenocarcinoma, and hepatocellular carcinoma demonstrated a high correlation between high expression levels of And-1 in tumors and poor prognosis. Thus, we hypothesized that And-1 is a novel target for anti-cancer treatment.

Figure 1B:
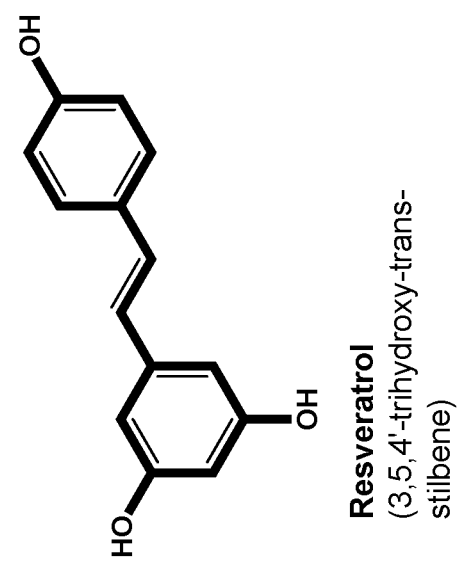
Figure 1B:
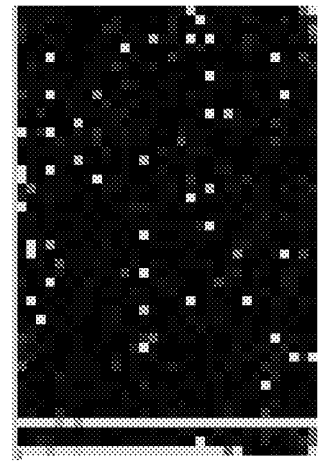
Figure 1B:
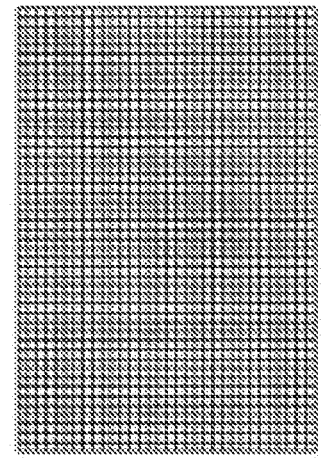

High-throughput drug screening was performed using a HEK-293T-And-1-Luc cell line expressing Luciferase fused to And-1 (FIG. 1A). The level of cellular Luciferase activity was reflective of the level of And-1 protein. In this screening, if a drug causes down-regulation of And-1 in cells, then the luciferase activity in the drug-treated cells will be reduced in comparison to cells that did not receive the drug treatment. In the drug screening assays, cells were treated with testing drugs for 48 hours. Resveratrol (3,5,4'-trihydroxy-trans-stilbene) was identified as a drug causing down-regulation of And-1 protein (FIG. 1B).

Figure 2:
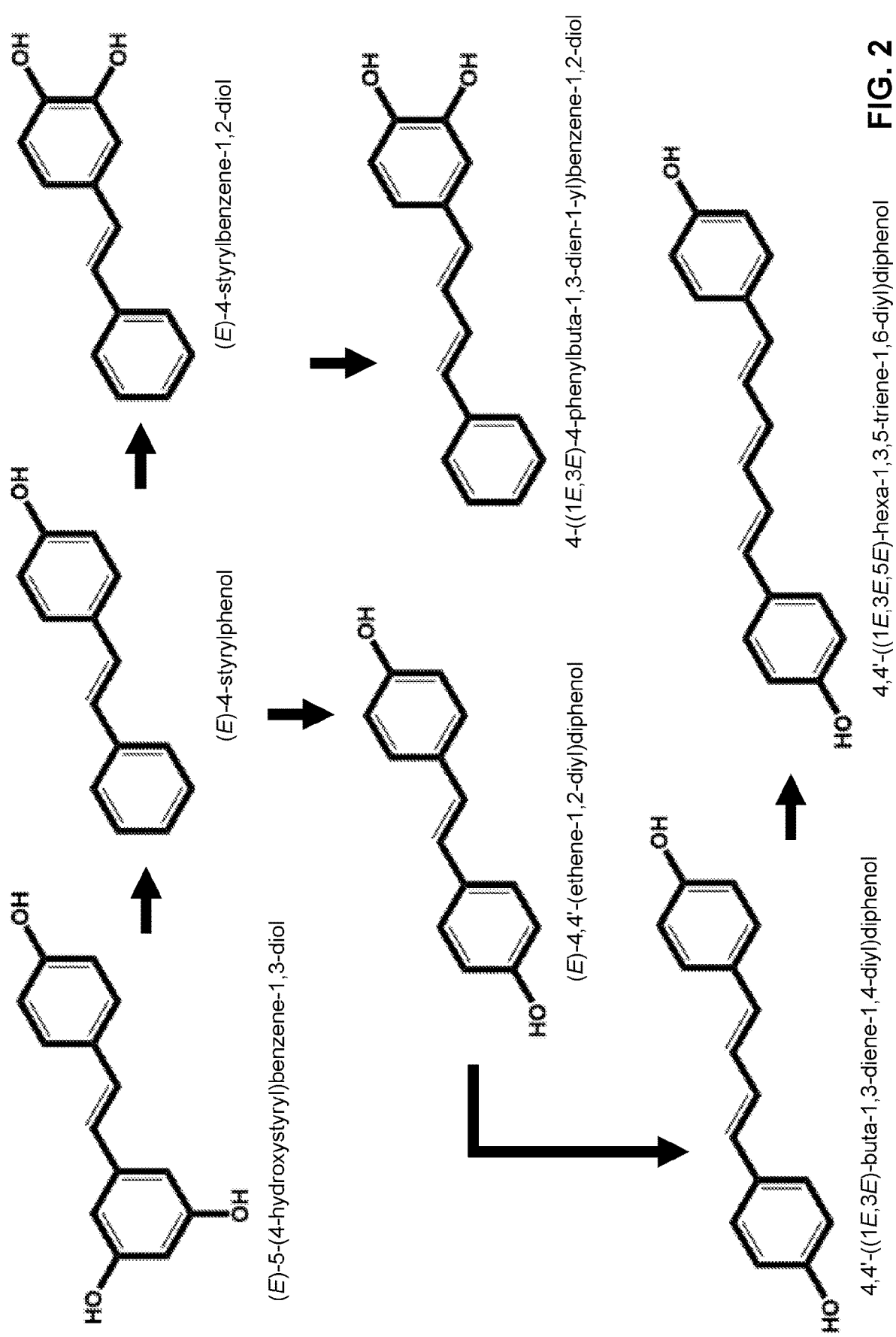
FIG. 2 shows chemical structures of resveratrol derivatives.

Based on identification of resveratrol as a lead compound in the drug screening assays, the anti-cancer activity of synthetic resveratrol analogs (FIG. 2) was next investigated and compared to resveratrol using HCT116 cells, U2OS cells, MDA-231/GFP cells, and PANC-1 cells. One analog, DHS, was found to be 10 times more potent than resveratrol according to the $IC_{50}$ values (Table 1).

The structure activity relationship (SAR) of the derivatives of resveratrol were considered. The data in Table 1 indicated that removal of R2 and R4 at A ring (Analog 3) did not improve potency (from 24.47~81.97 µM to 23.62~109.11 Based on Analog 3, further adding an —OH group at R7 (Analog 4) increased potency about one-fold (from 23.62~109.11 µM to 13.68~57.11 µM. The substitution of a —OH group on R3, DHS resulted in a large improvement in cytotoxicity (from 23.62~109.11 µM to 2.30~21.99 µM. Thus, the analysis indicated that the R3 site is more important than the R2 and R4 sites for cytotoxicity.

TABLE 1

Cytotoxicity of compounds against various cancer cells ($IC_{50}$, µM)

| Name | Structure | HCT116 | U2OS | MDA-231/GFP | PANC-1 |
| --- | --- | --- | --- | --- | --- |
| Resveratrol | 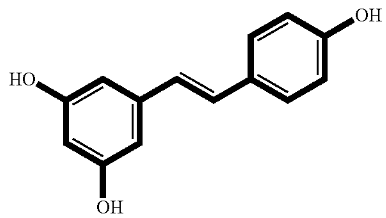 | 24.47 ± 3.32 | 30.21 ± 4.22 | 42.41 ± 4.90 | 81.97 ± 24.35 |
| DHS | 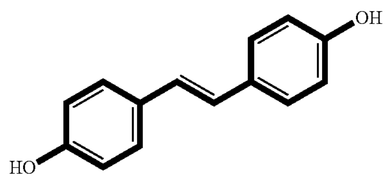 | 2.30 ± 0.78 | 1.23 ± 0.73 | 5.32 ± 3.38 | 21.99 ± 6.42 |
| #2 | 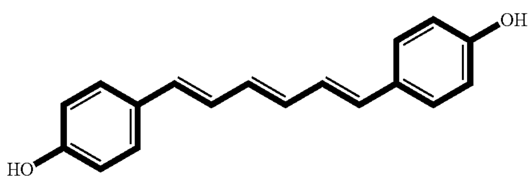 | 11.73 ± 6.46 | 0.37 ± 0.28 | 57.91 ± 15.38 | 122.58 ± 93.41 |
| #3 | 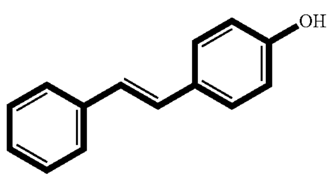 | 32.24 ± 5.88 | 23.62 ± 3.83 | 45.11 ± 13.93 | 109.11 ± 63.74 |
| #1 | 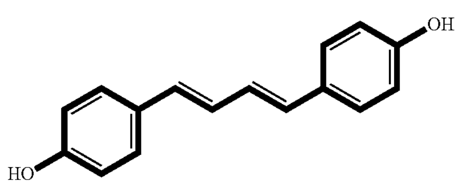 | 6.48 ± 3.98 | 1.10 ± 1.05 | 70.70 ± 16.72 | 307.91 ± 86.31 |
| #4 | 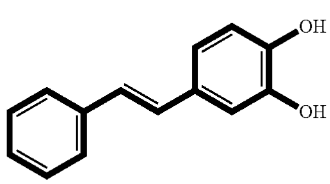 | 50.23 ± 9.72 | 33.59 ± 27.96 | 13.68 ± 2.98 | 57.11 ± 44.71 |

TABLE 1-continued

Cytotoxicity of compounds against various cancer cells (IC$_{50}$, μM)

| Name | Structure | HCT116 | U2OS | MDA-231/GFP | PANC-1 |
|---|---|---|---|---|---|
| #5 | (structure) | 9.50 ± 3.64 | 4.66 ± 2.67 | 5.47 ± 4.02 | 18.45 ± 8.87 |
| Hydroxyurea | | 305.67 ± 61.11 | 262.33 ± 181.05 | 704.25 | 2399.10 ± 484.82 |
| Gemcitabine | | 0.046 ± 0.041 | 0.51 ± 0.17 | 0.03 ± 0.04 | 7.43 ± 5.24 |
| Cisplatin | | 5.78 ± 1.24 | 14.21 ± 3.38 | 19.26 ± 9.50 | 5300.29 ± 535.93 |

Figure 3A:
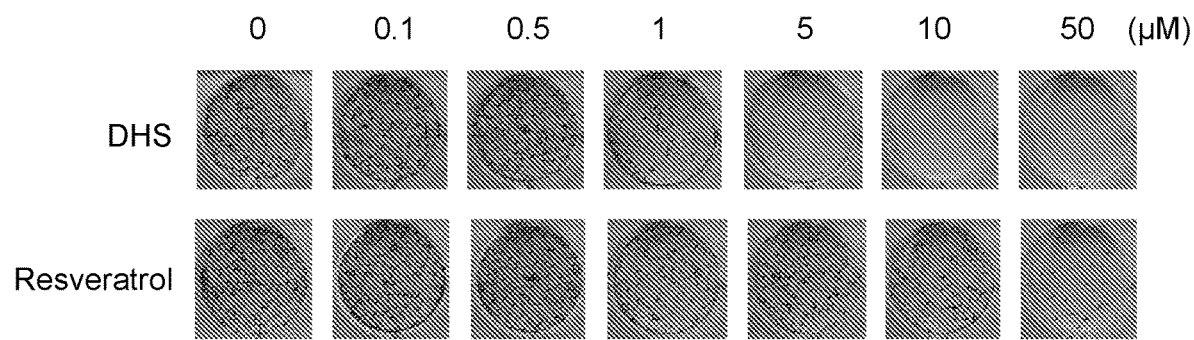
FIG. 3 shows that 4,4'-trans-dihydroxystilbene (DHS) can efficiently kill cancer cells by causing DNA damage. (A) Clonogenic colony formation assay showing colonies of HCT116 cells present after treatment with 0 to 50 μM DHS or resveratrol, and showing stronger suppression by DHS. (B) Graph showing quantitative results of colony formation assay. (C) Graph showing GI50 values (μM) for various cell lines (x-axis) treated with DHS or resveratrol.
Figure 3B:
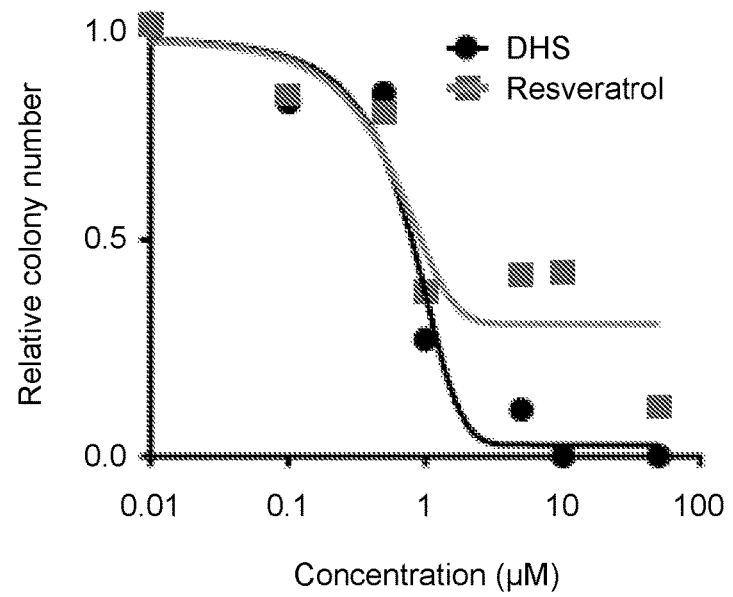
Figure 3C:
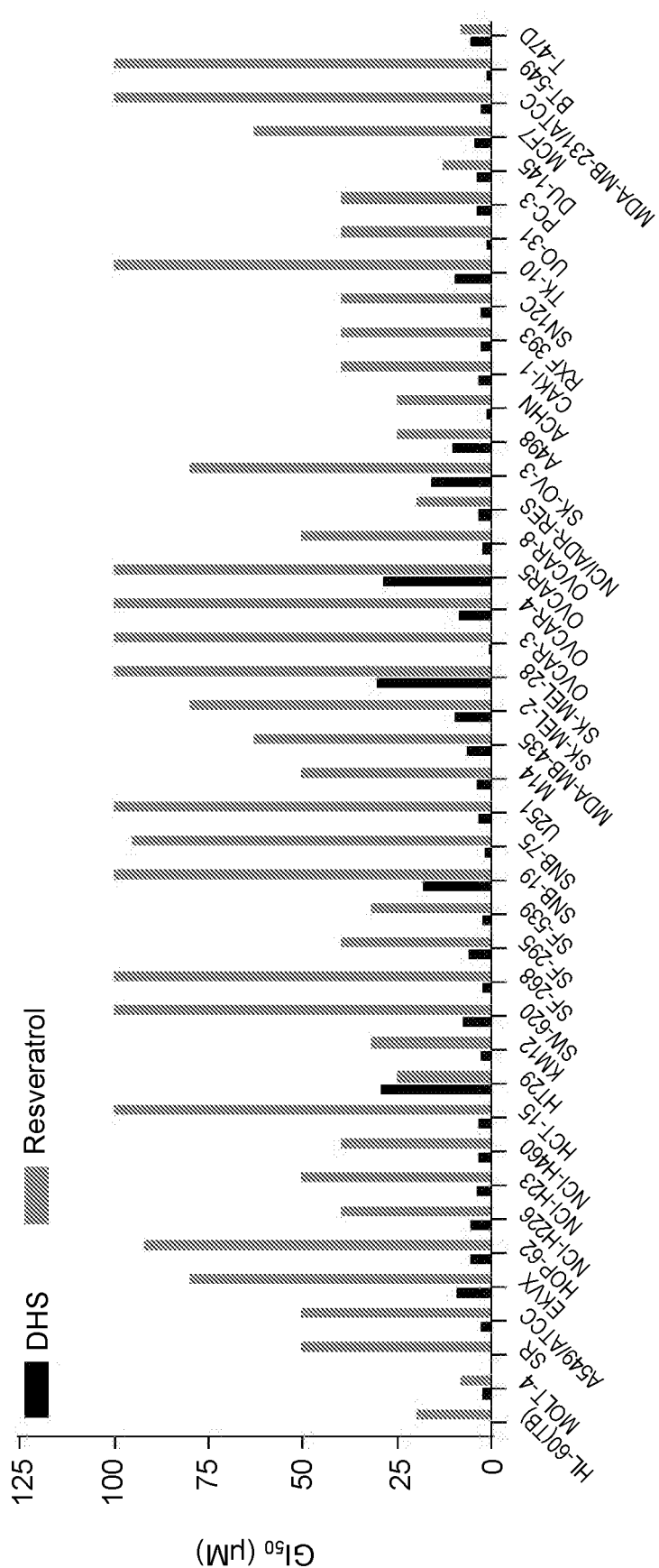

To confirm the cell killing effect of DHS, a clonogenic colony formation assay was conducted. It was found that DHS exhibited a stronger suppression effect on HCT116 cell colony formation than resveratrol (FIGS. 3A and 3B). The effect of DHS on growth of cancer cell lines was analyzed using The NCI Development Therapeutics Program (DTP). Among the cell lines analyzed, DHS was shown to have an improved effect on suppressing cancer cell growth as compared to resveratrol (FIG. 3C).

Example 2

Figure 4:
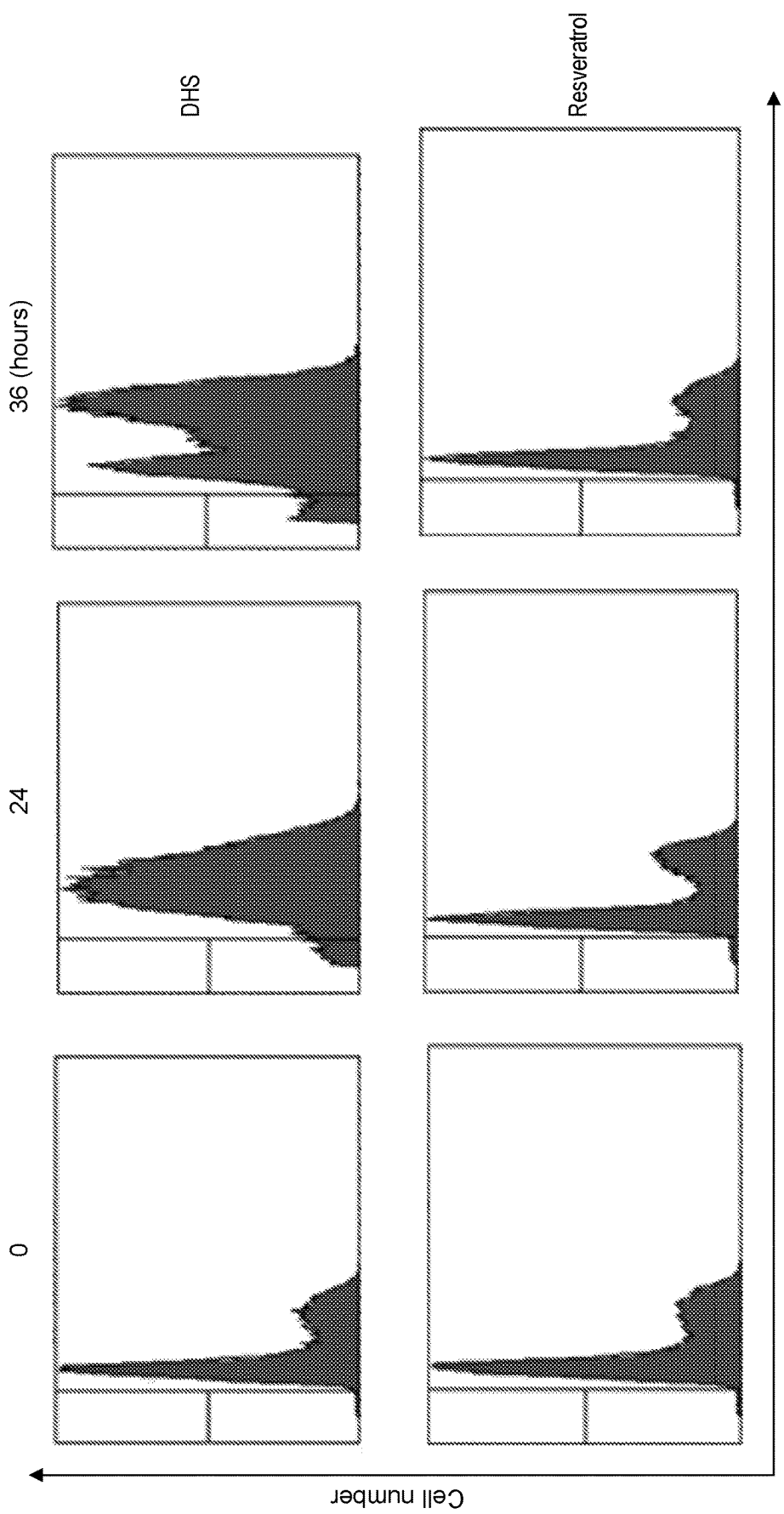
FIG. 4 shows that DHS arrests the cell cycle of HCT116 cells at S phase and inhibits DNA replication while resveratrol did not change the cell-cycle population at the same dose (10 μM).

DHS Causes DNA Damage, Cell Cycle Arrest at S Phase, Inhibition of Cell Replication, DNA Replication Fork Stalling, and dNTP Depletion A cell-cycle assay was conducted to study whether DHS would affect cell-cycle progression. DHS treatment resulted in a robust robust S-phase arrest in HCT116 cells, while resveratrol did not change the cell-cycle population at the same dose (10 μM; FIG. 4).

Figure 5A:
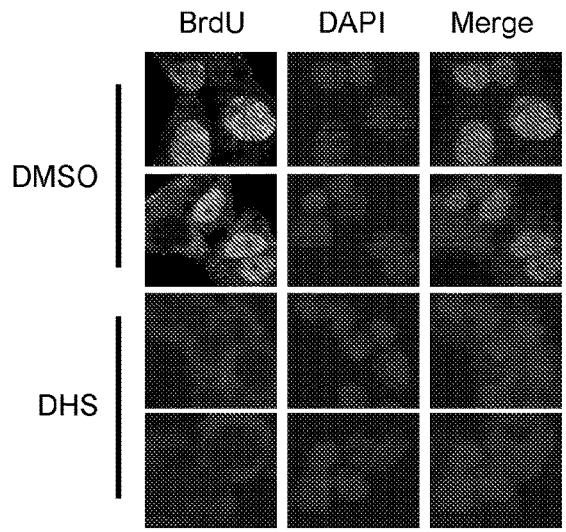
FIG. 5 shows that DHS represses DNA replication. (A) Immunoflourescent assay showing bromodeoxyuridine (BrdU) and 4',6-diamidino-2-phenylindole (DAPI) staining of HCT116 cells treated with dimethyl sulfoxide (DMSO; vehicle control) or DHS. "Merge" indicates that the BrdU and DAPI images were merged into a single image. (B) Fluorescence-activated cell sorting assay showing percentages of cells in S phase after treatment with DMSO or 1 to 20 μM DHS. RedF11 and BluF11 indicate red and blue fluorochromes used in cell sorting, respectively.
Figure 5B:
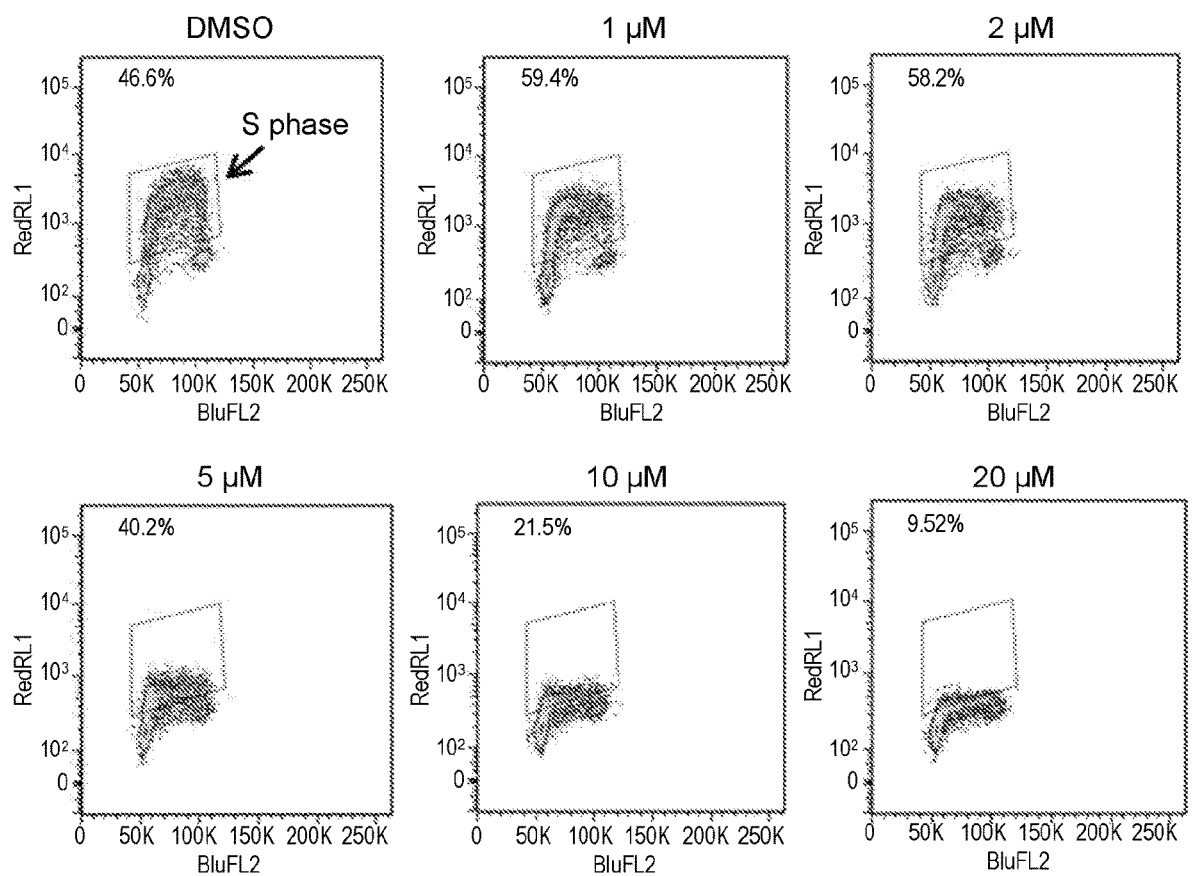

To test whether DHS can repress DNA replication, BrdU incorporation was examined using an immunofluorescent assay. It was found that BrdU intensity was decreased in DHS-treated HCT116 cells (FIG. 5A). BrdU incorporation was tracked by fluorescence-activated cell sorting (FACS). It was found that the treatment with DHS not only arrested cells at S phase but also inhibited BrdU incorporation from 46.6% to 9.52% (FIG. 5B). Therefore, the data indicated that DHS suppresses cancer cell growth by blocking DNA replication.

Figure 6A:
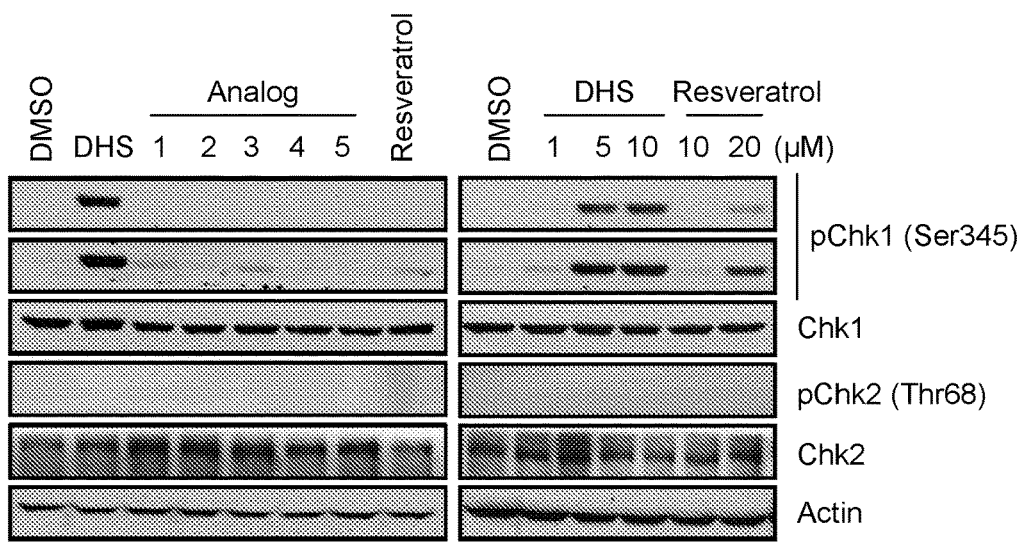
FIG. 6 shows that treatment with DHS triggers DNA damage. (A) Western blots of DNA damage markers p-Chk1 (Ser345=phosphorylated serine at position 345 of the amino acid sequence), Chk1, pChk2 (Thr68=phosphorylated threonine at position 68 of the amino acid sequence), and Chk2 as well as an Actin control. The left blot shows markers after treatment with DMSO, DHS (10 μM), analogs 1-5 as shown in FIG. 2, and resveratrol. The right blot shows markers after treatment with DHS and resveratrol in the indicated amounts and DMSO. (B) Comet assay showing induction of DNA double strand breaks by DHS (2.5 μM) as seen by increased lengths of tail moments versus DMSO control at 24 hours. (C) Graph showing relative lengths of tail moments in the comet assay of (B). (D) Immunofluorescent assay showing increased levels of phosphorylated histone 2AX (i.e., γH2AX, a marker of DNA damage) after treatment with DHS (10 μM), resveratrol, or DMSO. DAPI and Merge are as described for FIG. 5(A).
Figure 6B:
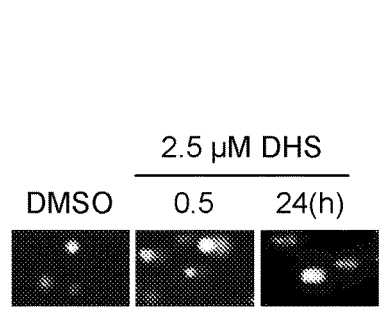
Figure 6C:
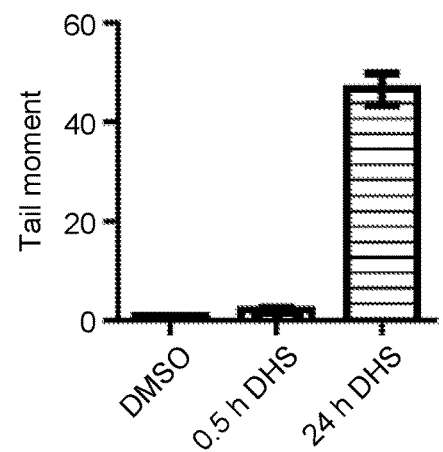
Figure 6D:
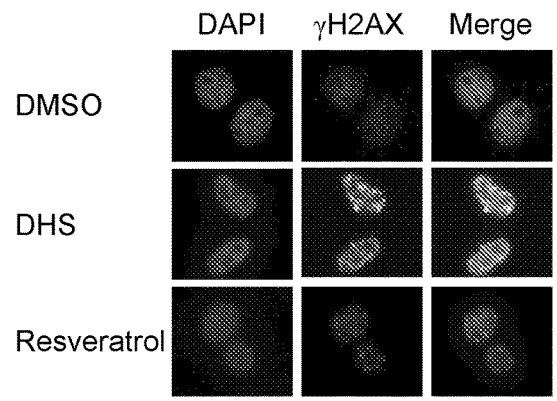

To investigate whether inhibition of DNA replication by DHS can trigger DNA damage, the DNA damage markers phosphor-Chk1 (pChk1, Serine 345) and phosphor-Chk2 (pChk2, Threonine 68) were analyzed in DHS-treated HCT116 cells. DHS (10 μM for 20 minutes) was more potent than resveratrol and the other analogs in its ability to cause DNA damage as shown by the higher amounts of phosphorylated CHK1 (CHK1 pSerine 345) in cells treated with DHS (FIG. 6A). The other analogs did not cause DNA damage (FIG. 6A). A comet assay was next used to test if DNA double strand breaks are induced by DHS. Treatment of HCT116 cells with DHS (2.5 μM for 24 hours) caused significant DNA double strand breaks as shown by increased lengths of tail moments (FIGS. 6B-C). Increased levels of phosphorylated histone 2AX (i.e., γH2AX, a marker of DNA damage) were also detected by immunostaining in HCT116 cells treated with DHS at a dosage of 10 μM for 12 hours (FIG. 6C), further confirming that DHS significantly induces DNA damage.

Figure 7B:
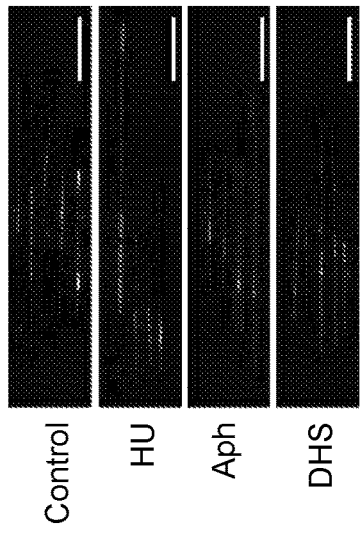
FIG. 7 shows that DHS inhibits DNA replication by DNA replication fork stalling. (A) Diagram showing the procedure of performing the DNA fiber experiment. Compound treatment indicates treatment with DMSO (Control), DHS, hydroxyurea (HU), or Aphidicolin (Aph) 2 hours prior to adding iododeoxyuridine (IdU) for indication of replication stalling and chlorodeoxyuridine (CldU) for indication of newly initiated replication origins. (B) Images showing iododeoxyuridine (IdU) and chlorodeoxyuridine (CldU) signaling, and that treatment of DHS causes DNA replication stalling. The quantitative results of folk speed (kb/min) and percentages of red-only (i.e., IdU) tracks are shown as (C) and (D), respectively.
Figure 7D:
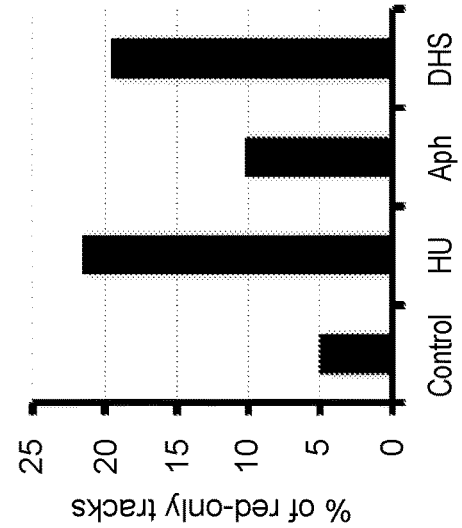
Figure 7A:
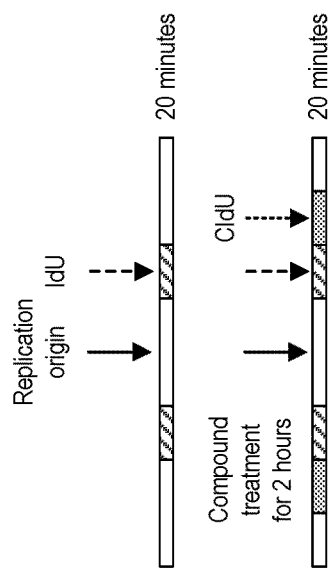
Figure 7C:
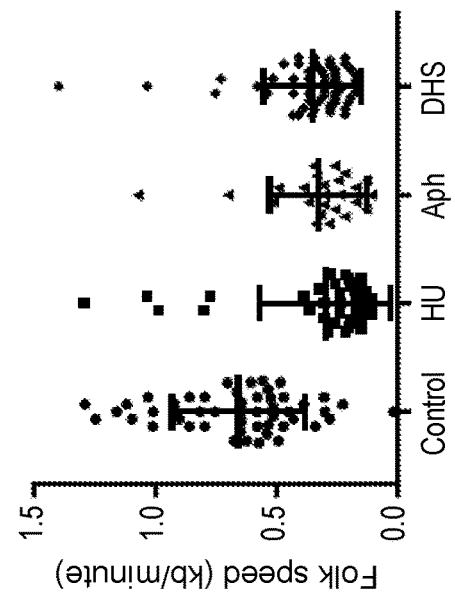

We previously demonstrated that depletion of And-1 in cells causes DNA replication fork stalling (Hao et al., 2015). Thus, the effect of DHS on DNA replication and cell cycle progression was investigated. Replication fork speeds were examined by DNA fiber assay (FIG. 7A). Briefly, DHS, hydroxyurea (Hu), or Aphidicolin (Aph) was added to HCT116 cells 2 hours prior to labeling of DNA with iododeoxyuridine (IdU) and/or chlorodeoxyuridine (CldU). Treatment with DHS dramatically caused DNA replication stalling, as did treatments with Aph and Hu (FIG. 7B). The rate of replication fork progression (folk speed) was significantly reduced in DHS-treated cells (FIG. 7C). Analysis of replication labeling with chlorodeoxyuridine (CldU) (FIG. 7D) also showed that DHS treatment blocks DNA replication.

Figure 8A:
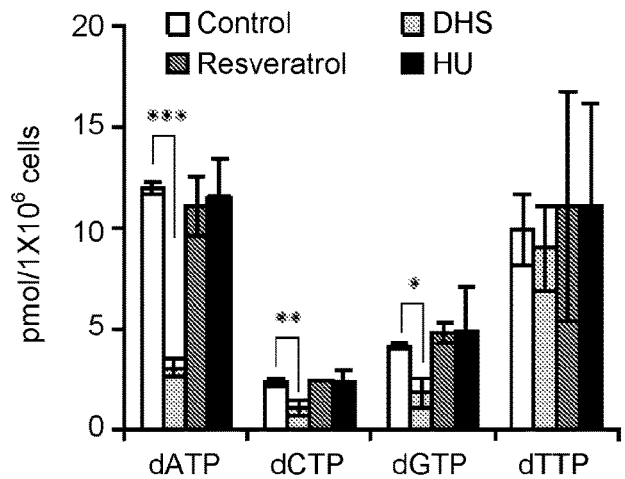
FIG. 8 shows that DHS suppresses dNTP synthesis. (A) Graph showing amount of dNTPs in HCT116 cells following treatment with resveratrol, DHS, HU, or control (DMSO). (B) Graph showing relative level of dNTPs in HCT116 cells treated with DHS for 2 hours or 24 hours as compared to control. (C) Graph showing the amount of dATP in HCT116 cells after treatment with increasing dosages of DHS.
Figure 8B:
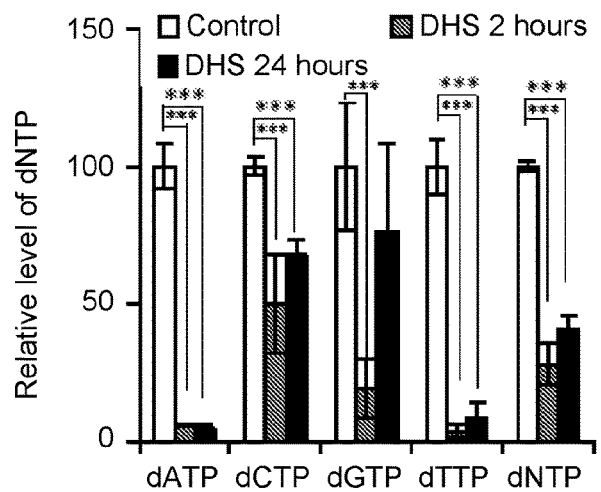
Figure 8C:
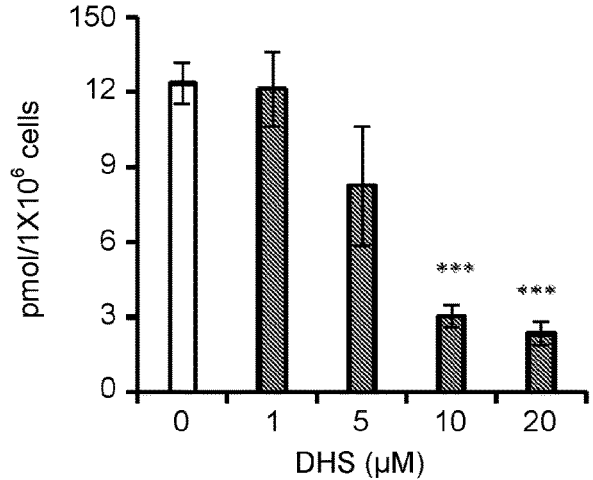

The effect of DHS on dNTP synthesis was investigated by measuring the amount of dNTPs in DHS-treated HCT116 cells. It was found that DHS inhibited synthesis of dATP, dCTP, dGTP, and dTTP, whereas resveratrol and Hu did not (FIGS. 8A-B). The effect of DHS treatment on production of dATP, for example, was shown to be dose dependent (1 to 20 μM DHS; FIG. 8C).

Example 3

DHS Down Regulates And-1, RRM1, and RRM2 Proteins and Binds to RRM2

Figure 9A:
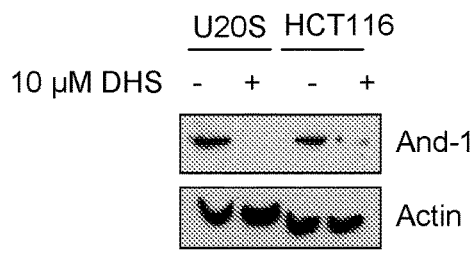
FIG. 9 shows that treatment with DHS down-regulates levels of And-1, ribonucleotide reductase subunit 1 (RRM1), and ribonucleotide reductase subunit 2 (RRM2) proteins by ubiquitin proteasome pathway. (A) Western blot showing And-1 and Actin (control) protein levels in U2OS and HCT116 cells after treatment with 10 DHS. (B) Western blot showing RRM1, RRM2, and Actin (control) protein levels in HCT116 cells after treatment with DHS and DMSO. (C) Graph showing percent cell viability in HCT116 cells and DHS-resistant HCT116 cells (i.e., HCT116-DHS-R) per log DHS concentration (μM). (D) Western blot showing DNA replication proteins (And-1, RRM2, RRM1, polymerase α)
Figure 9B:
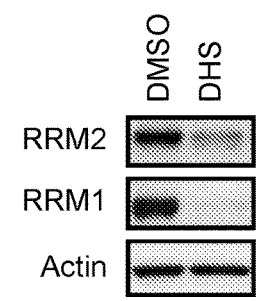

The effect of DHS treatment on And-1, RRM1, and RRM2 expression was investigated. DHS caused down-regulation of And-1 protein in both U2OS and HCT116 cells (FIG. 9A), and the effect was more potent than resveratrol (data not shown). DHS also caused down-regulation of RRM1 and RRM2 proteins in DHS-treated HCT116 cells (FIG. 9B).

Figure 9C:
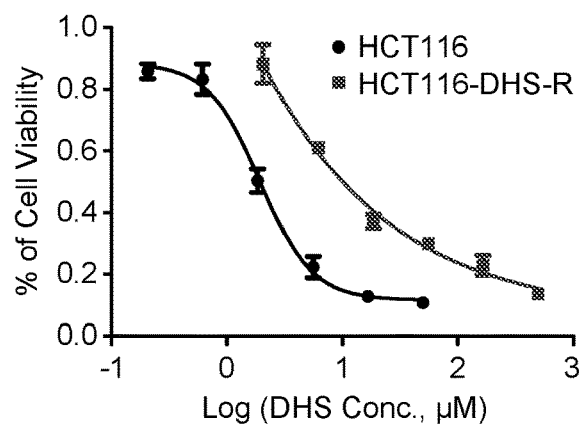
Figure 9D:
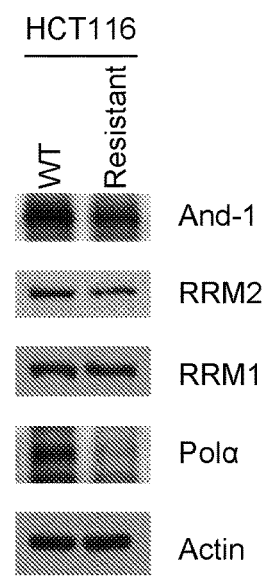
Figure 9E:
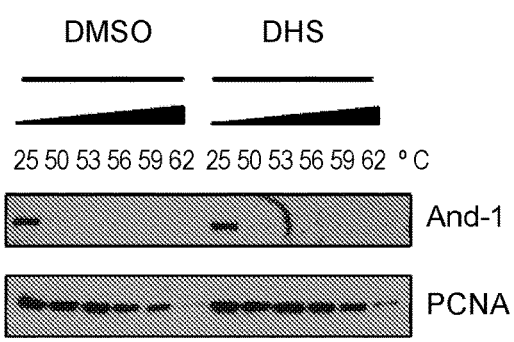
Figure 9F:
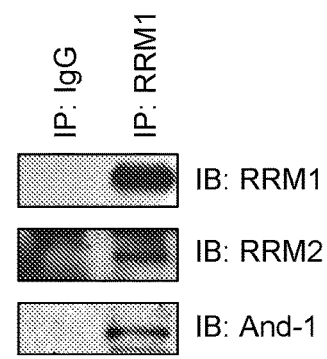

In order to study the mechanisms by which DHS induces down-regulation of And-1, RRM1, and RRM2 proteins, DHS-resistant HCT116 cells were generated (FIG. 9C). FIG. 9D shows that DHS treatment results in decreased levels of And-1, RRM1, RRM2, and Polymerase α, indicating that DHS suppresses DNA replication proteins. Next, it was investigated whether DHS directly binds to And-1, RRM1, or RRM2. A cellular thermal shift assay (Jafari et al., 2014) was conducted for And-1 (FIG. 9E). The equal amount of And-1 protein in DMSO- or DHS-treated groups indicated that DHS does not bind to And-1. A coimmunoprecipitation (CoIP) assay was conducted to determine whether And-1, RRM1, and RRM2 interact in the same complex. The result implied that DHS interacts with RRM1 or RRM2 (FIG. 9F).

Figure 12A:
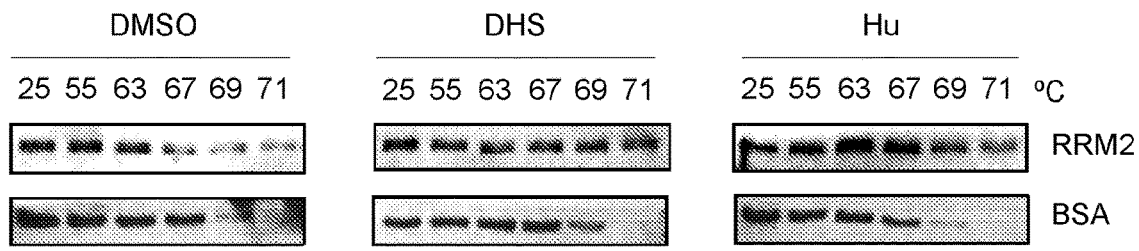
Figure 12B:
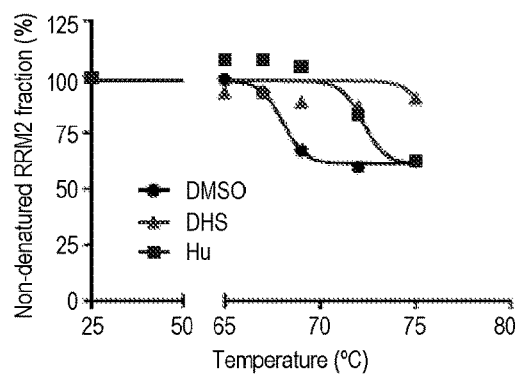
Figure 12C:
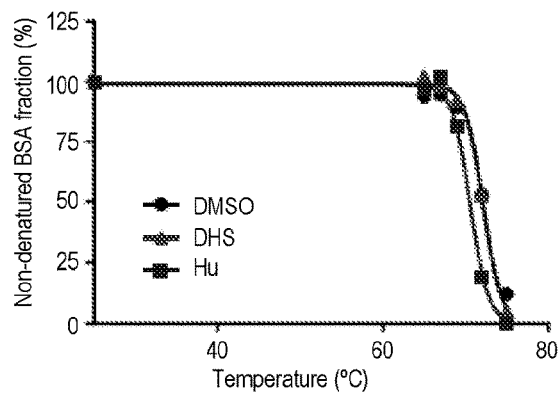

To investigate binding of DHS to RRM1 and RRM2, a thermal shift assay was performed in HCT116 cells treated with DMSO (vehicle), resveratrol, DHS, gemcitabine, or hydroxyurea (Hu). Gemcitabine is known to bind RRM1 (Plunkett et al., 1995 and Chen et al., 2011), and Hu has been reported to bind RRM2 (Thelander et al., 1985). In accordance with reported binding, gemcitabine-treated samples showed robust levels of RRM1 and Hu-treated samples showed robust levels of RRM2 (FIG. 10A). Additionally, robust levels of RRM2 were found in DHS-treated HCT116 cells, indicating that DHS binds to RRM2 (FIG. 10A). DHS stabilized RRM2 protein in a dose responsive manner (5 to 20 µM DHS; FIG. 11A). To rule out nonspecific effects of DHS on RRM2, an in vitro thermal shift assay was conducted. Purified RRM1 and RRM2 were mixed and then incubated with DHS or Hu for 4 hours before performing the assay. It was found that DHS stabilized purified RRM2 protein after high temperature incubation (FIG. 12A).

To study the binding site of DHS on RRM2 protein, the RRM2-DHS interaction was simulated using virtual docking analysis (www.dockingserver.com). The structure of RRM2 protein (2UW2) was retrieved from the Protein Database (PDB). The simulation result showed that DHS is expected to bind at residues VAL146, SER150, GLN151, THR156, ARG159, CYS160, and ILE166 of RRM2. The estimated free energy of binding was −2.91 kcal/mol (Table 2).

TABLE 2

Docking of DHS and RRM2.

| | |
|---|---|
| Est. Free Energy of Binding | −2.91 kcal/mol |
| Est. Inhibition Constant, Ki | 7.31 mM |
| vdW + Hbond + desolv Energy | −4.06 kcal/mol |
| Electrostatic Energy | −0.03 kcal/mol |
| Total Intermolec. Energy | −4.09 kcal/mol |
| Frequency | 10% |
| Interact. Surface | 477.308 |

Figure 12D:
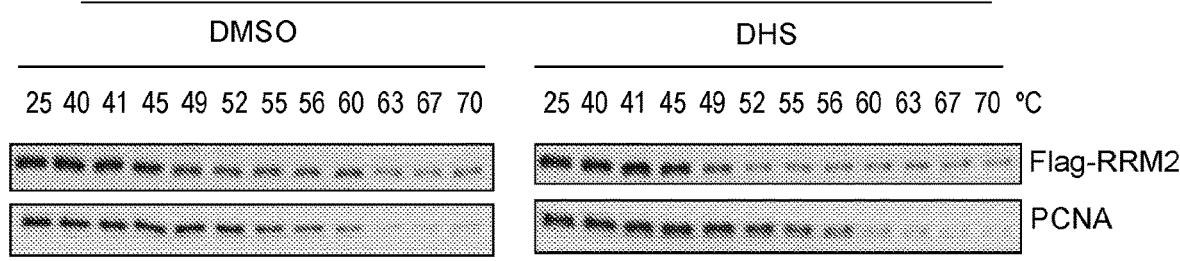
Figure 12E:
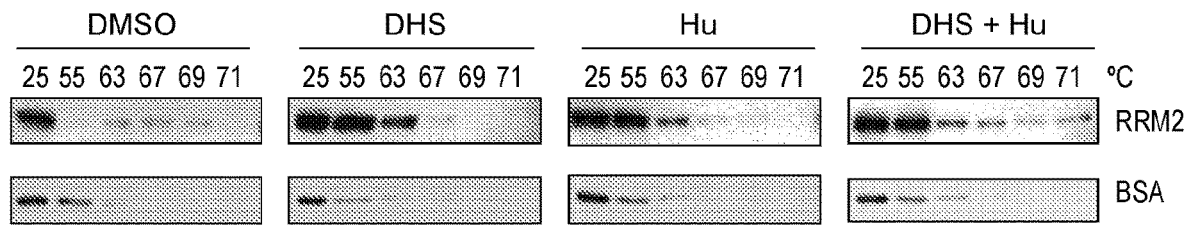
Figure 12F:
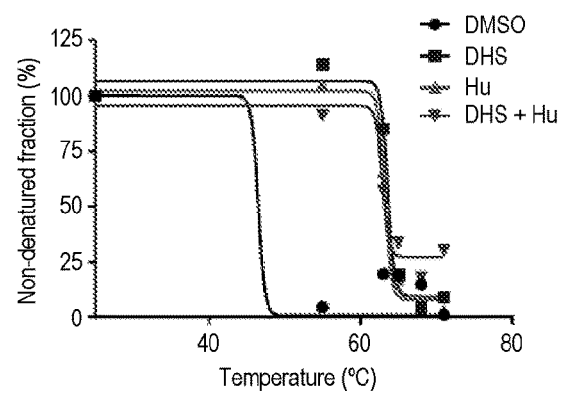
Figure 12G:
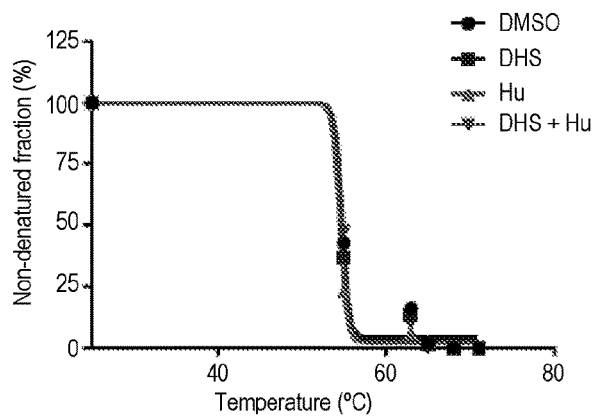

To verify the DHS binding site on RRM2, a RRM2 construct with a deletion of GLU147 to ILE166 was generated. It was found that DHS was not able to maintain thermal stability of the truncated-RRM2 protein (FIG. 12D). Since Hu is also known to interact with RRM2 protein, the effect of DHS on Hu binding to RRM2 was investigated using a cellular thermal shift assay with KB-Hu (an Hu resistant oral cancer cell line). It was found that DHS further stabilized RRM2 protein in combination with Hu as compared to single treatments with either DHS or Hu alone, indicating that DHS and Hu bind to RRM2 at different sites (FIG. 12E).

Figure 13A:
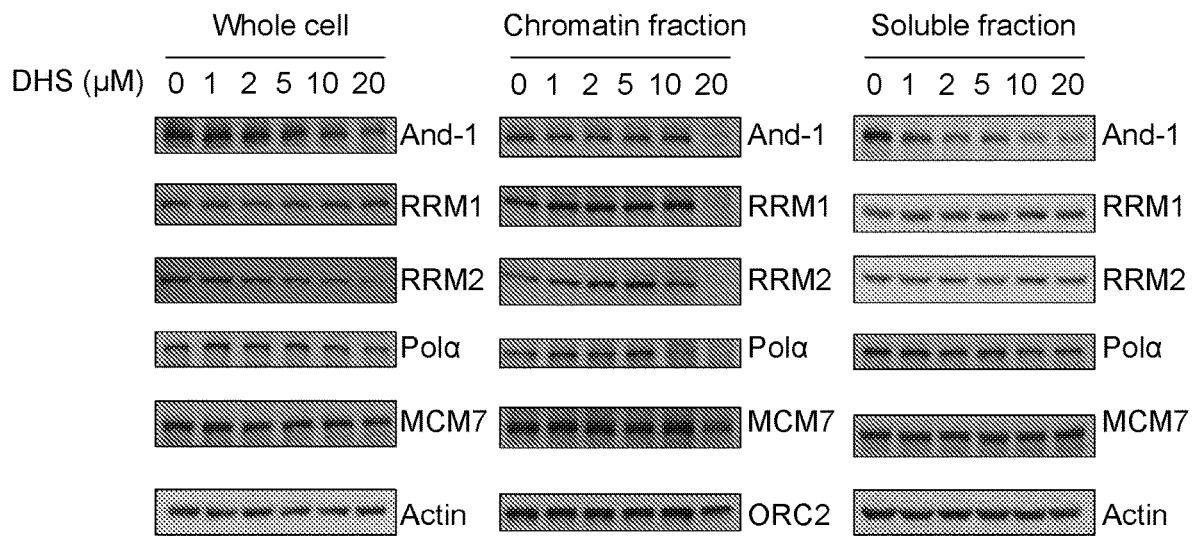
Figure 13B:
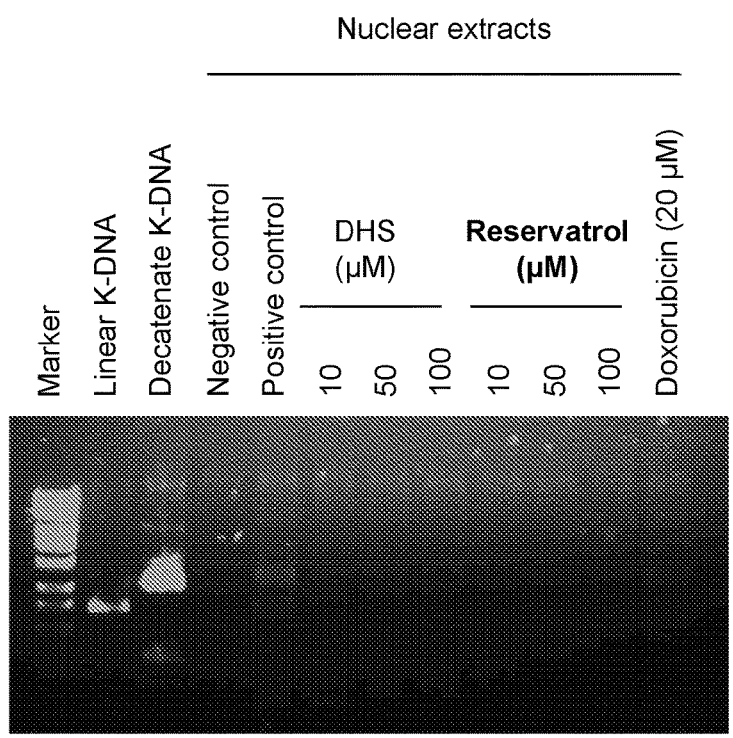

In addition, resveratrol has been previously reported to interact with DNA grooves (Usha et al., 2006). FIG. 13A shows that DHS treatment of HCT116 cells resulted in dissociation of And-1, RRM1, RRM2, MCM1, and Polymerase α from chromatin, indicating DHS might affect DNA structure. A similar result with And-1, RRM1, and RRM2 was also observed in DHS resistant HCT116 cells (data not shown). Additionally, incubation of DHS with plasmid DNA resulted in increased UV absorption, further indicating that DHS binds to DNA. Incubation of DHS with kDNA also resulted in reduced bonds of decatenate K-DNA, demonstrating that DHS inhibits Topoisomerase II activity via direct interactions with DNA (FIG. 13B).

Example 4

Figure 14A:
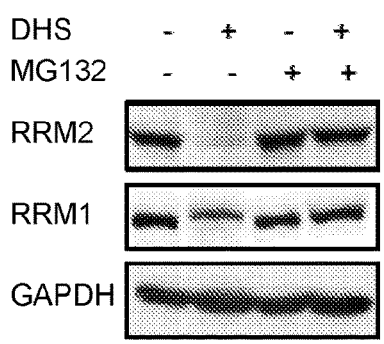
Figure 14B:
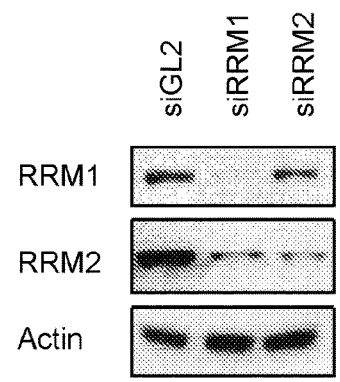
Figure 14C:
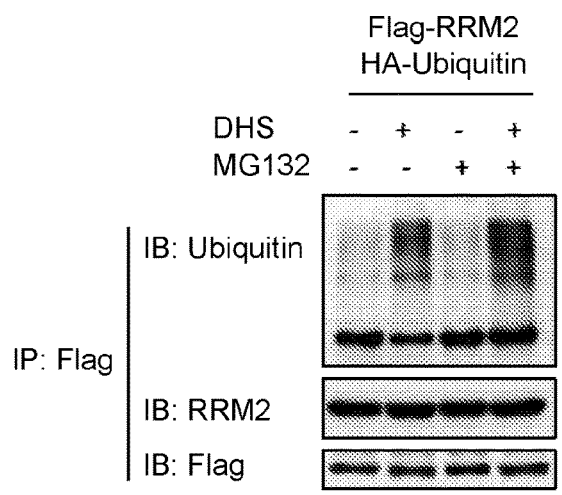
Figure 14D:
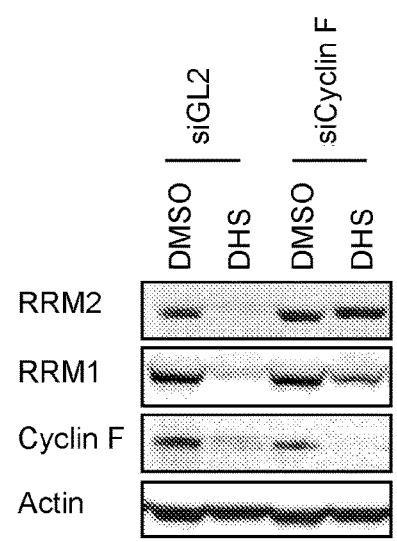
Figure 14E:
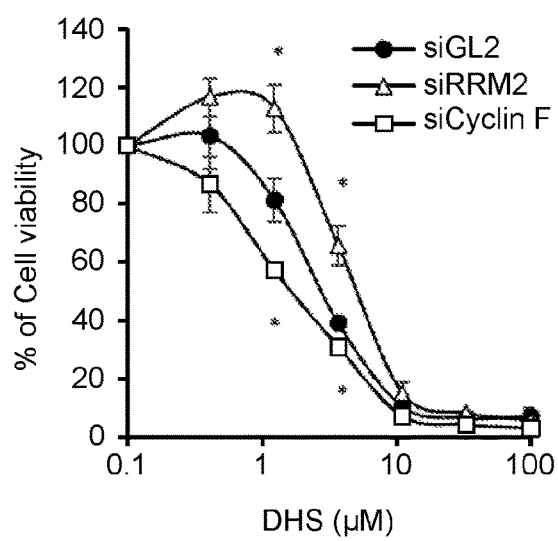

DHS Induces RRM2 Protein Degradation Via Cyclin F Proteasome Degradation Pathway It was next investigated whether treatment with DHS leads to reduced levels of RRM2 through the proteasome degradation pathway. It was found that both RRM2 and RRM1 levels in HCT116 cells were rescued by treatment with the proteasome inhibitor MG-132 prior to DHS treatment (FIG. 14A). Similar rescue of And-1 levels was observed in HCT116 cells treated with MG-132 prior to DHS (data not shown). To confirm whether degradation of RRM1 is dependent on RRM2, RRM1 or RRM2 expression was knocked down by treatment with siRNAs and resultant protein amounts were detected. It was found that depletion of RRM2 resulted in reduced amounts of RRM1 (FIG. 14B). It was also found that depletion of RRM1 resulted in reduced amounts of RRM2, suggesting that the holoenzyme, RNR, is required to exist for both RRM1 and RRM2. Next, a ubiquitination assay with MG-132 pre-treatment was performed to determine whether a ubiquitination reaction is involved in DHS-mediated RRM2 degradation. It was found that ubiquitinated RRM2 was increased by DHS treatment and accumulated in the MG-132 pretreated sample (FIG. 14C). According to the literature, Cyclin F is the E3 ligase that ubiquitinates RRM2 (D'Angiolella et al., 2012). Thus, the amount of RRM2 in cells was determined after knockdown of Cyclin F by siRNA. It was found that knockdown of Cyclin F rescued the levels of RRM2 after treatment with DHS (FIG. 14D). Cell viability after DHS exposure was also investigated in cells in which either RRM2 or Cyclin F expression was knocked down by siRNA. It was found that Cyclin F-depleted cells were sensitive to DHS, while RRM2-depleted cells became less sensitive to DHS (FIG. 14E).

Example 5

DHS Overcomes Gemcitabine and Hu Resistance in Oral Cancer Cells

Figure 15A:
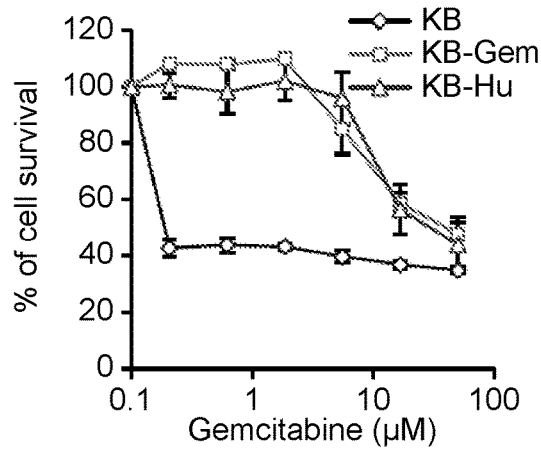
Figure 15B:
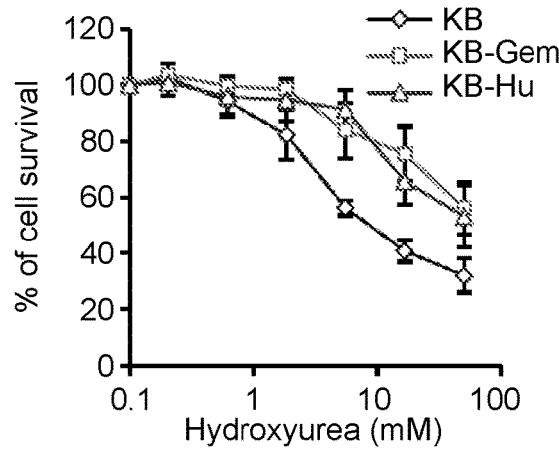
Figure 15C:
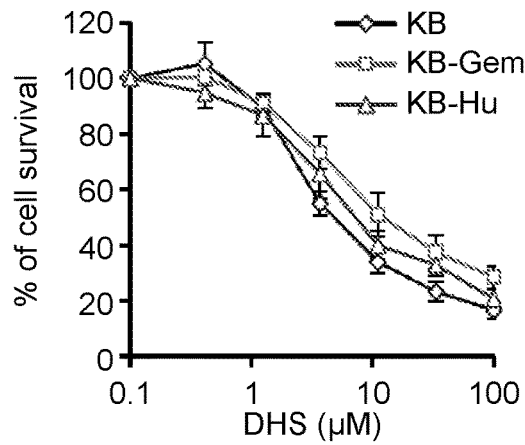
Figure 15D:
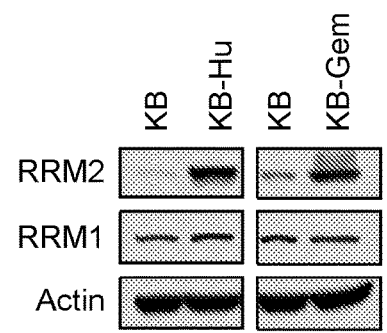

An oral cancer cell line, KB, and its gemcitabine-resistant and hydroxyurea resistant sublines, KB-Gem and KB-Hu, respectively, were treated with gemcitabine (FIG. 15A), hydroxyurea (FIG. 15B), or DHS (FIG. 15C). The results showed that treatment with DHS overcame gemcitabine and hydroxyurea resistance. Additionally, both KB-Gem and KB-Hu were found to overexpress RRM2 (FIG. 15D).

Figure 16B:
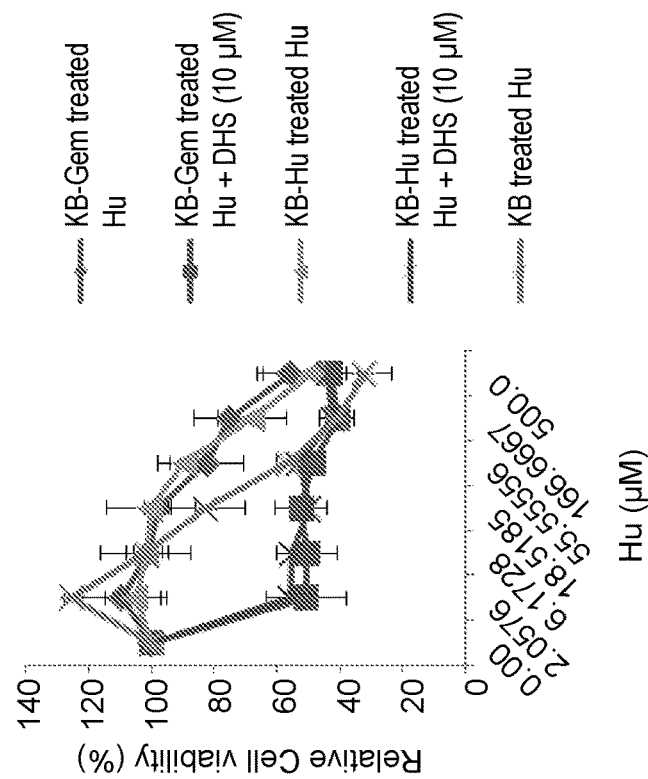
Figure 16A:
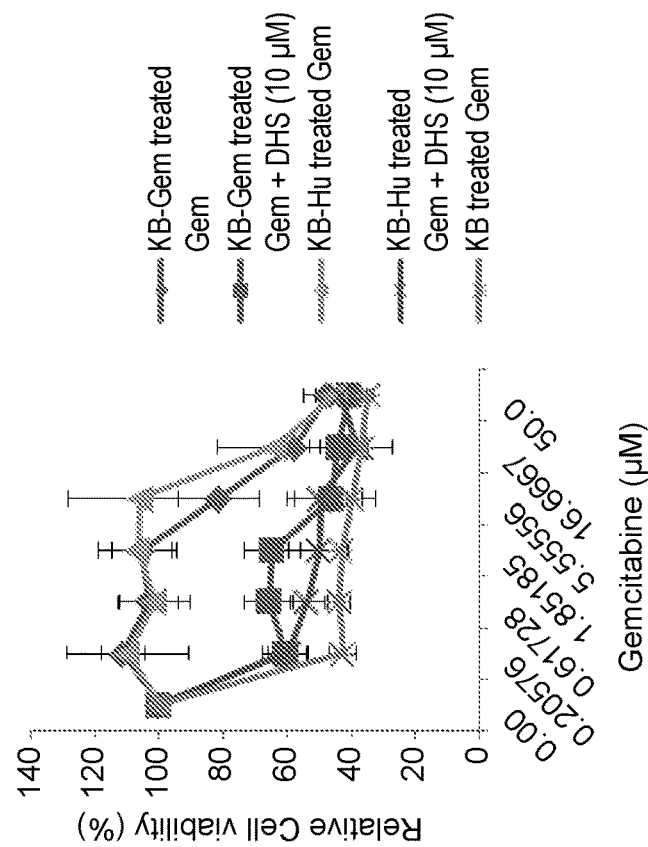
Figure 16D:
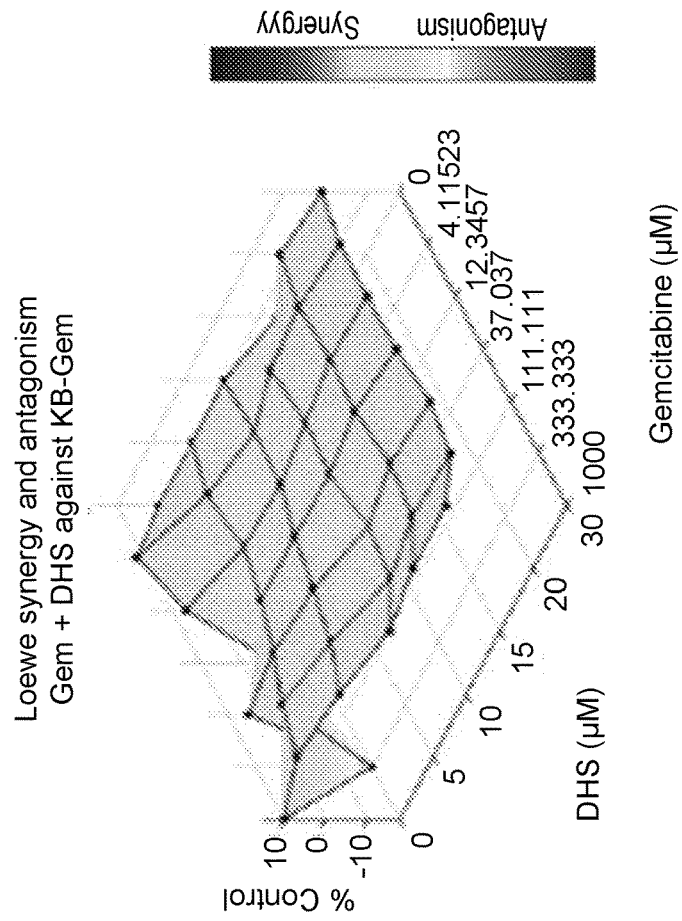
Figure 16C:
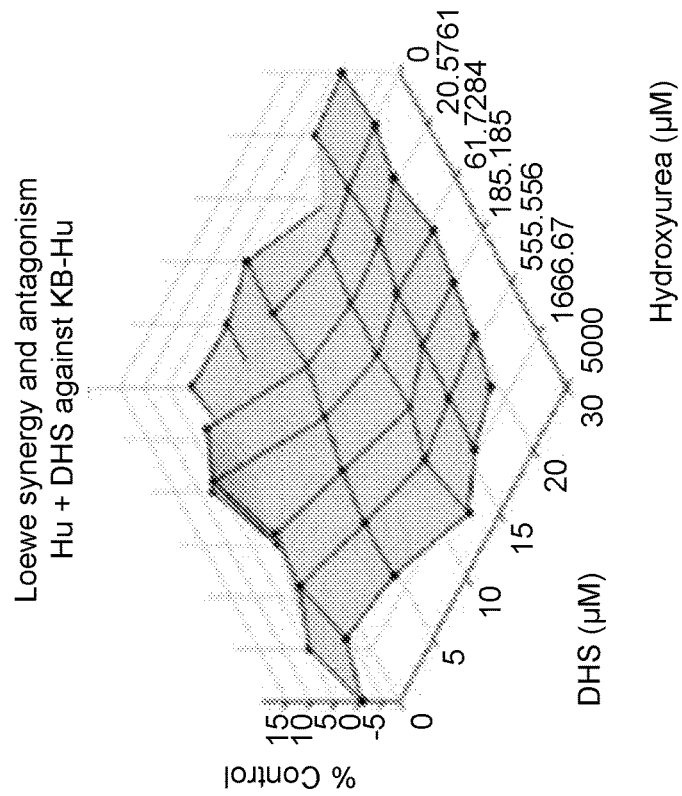

Next, the effect of combined treatment with DHS and Gemcitabine or Hydroxyurea was investigated. The presence of DHS resensitized cultured KB-gem and KB-Hu cell lines to gemcitabine and hydroxyurea (FIGS. 16A and 16B, respectively). And, it was found that the combinations demonstrated synergy against resistant cells, with combination indexes (CI) being lower than 1 at most of the dosages (FIG. 16C and Tables 3-7).

TABLE 3

CI for KB-Gem cells treated with DHS and Gem

| Gem against KB-Gem | DHS against KB-Gem | Effect | CI |
|---|---|---|---|
| 50.0 | 10.0 | 0.43294 | 1.12002 |
| 16.6667 | 10.0 | 0.38438 | 0.61524 |
| 5.55556 | 10.0 | 0.49601 | 0.87533 |
| 1.85185 | 10.0 | 0.50175 | 0.85554 |

TABLE 3-continued

CI for KB-Gem cells treated with DHS and Gem

| Gem against KB-Gem | DHS against KB-Gem | Effect | CI |
|---|---|---|---|
| 0.61728 | 10.0 | 0.53964 | 1.02061 |
| 0.20576 | 10.0 | 0.59862 | 1.38256 |

TABLE 4

CI for KB-Hu cells treated with DHS and Gem

| Gem against KB-Hu | DHS against KB-Hu | Effect | CI |
|---|---|---|---|
| 50.0 | 10.0 | 0.43294 | 1.12002 |
| 16.6667 | 10.0 | 0.38438 | 0.61524 |
| 5.55556 | 10.0 | 0.49601 | 0.87533 |
| 1.85185 | 10.0 | 0.50175 | 0.85554 |
| 0.61728 | 10.0 | 0.53964 | 1.02061 |
| 0.20576 | 10.0 | 0.59862 | 1.38256 |

TABLE 6

CI for KB-Gem cells treated with DHS and Hu

| Hu against KB-Gem | DHS against KB-Gem | Effect | CI |
|---|---|---|---|
| 500.0 | 10.0 | 0.43073 | 2.07108 |
| 166.667 | 10.0 | 0.40730 | 0.91622 |
| 55.5556 | 10.0 | 0.48494 | 0.65661 |
| 18.5185 | 10.0 | 0.52368 | 0.56493 |
| 0.61728 | 10.0 | 0.50408 | 0.47444 |
| 0.20576 | 10.0 | 0.50642 | 0.47527 |

TABLE 7

CI for KB-Hu cells treated with DHS and Hu

| Hu against KB-Hu | DHS against KB-Hu | Effect | CI |
|---|---|---|---|
| 500.0 | 10.0 | 0.43804 | 1.87059 |
| 166.667 | 10.0 | 0.42295 | 0.96782 |
| 55.5556 | 10.0 | 0.52994 | 1.1261 |
| 18.5185 | 10.0 | 0.49666 | 0.86332 |
| 0.61728 | 10.0 | 0.5522 | 1.08263 |
| 2.05761 | 10.0 | 0.55784 | 1.1192 |

Example 6

DHS Overcomes Gemcitabine Resistance in Pancreatic Cancer Cells

Figure 17A:
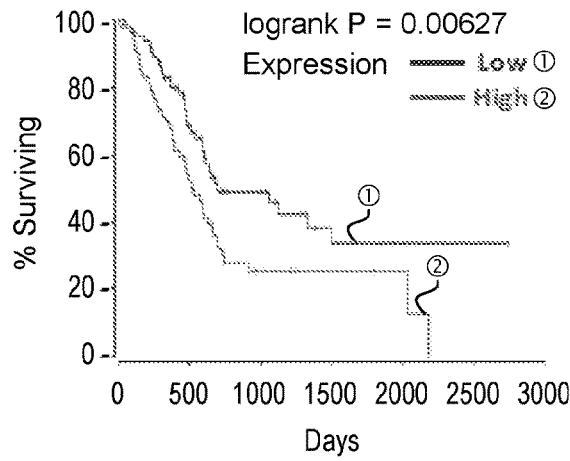
Figure 17B:
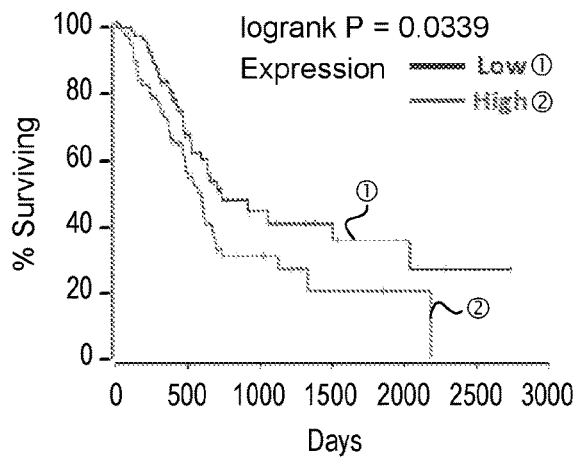
Figure 17C:
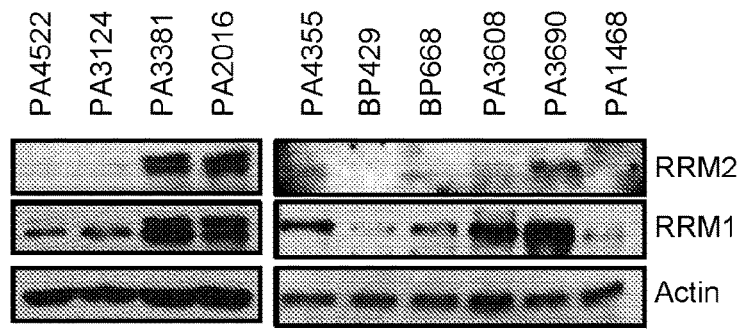
Figure 17D:
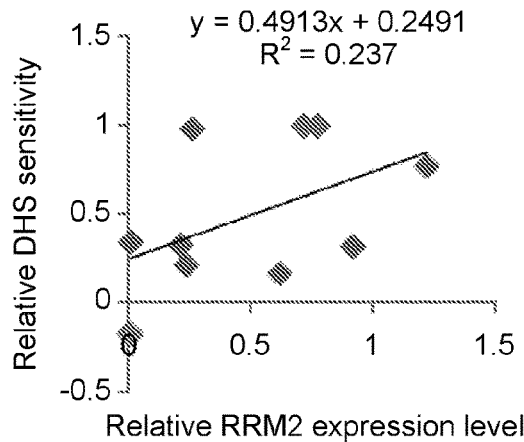
Figure 17E:
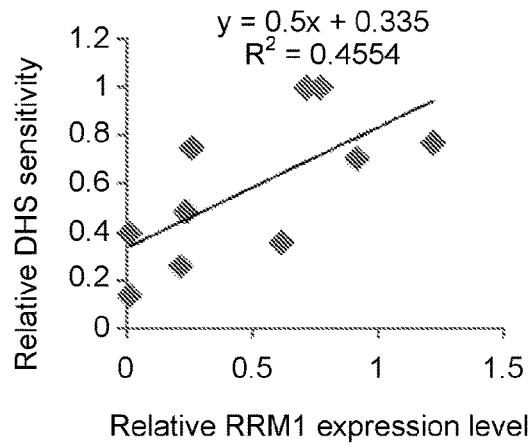

The correlation between expression levels of RRM2/RRM1 and survival rates of pancreatic cancer patients was investigated. It was found that patients with highly expressed RRM2 or RRM1 have poor survival rates (FIGS. 17A-B). Based on this finding, it was determined whether DHS could suppress high-RRM1/RRM2 levels in cells with mouse-derived pancreatic tumor cells. RRM1 and RRM2 levels in the pancreatic tumor cells was determined (FIG. 17C). Cell viability assays were then performed to determine DHS efficacy in terms of cytotoxicity. It was found that RRM2/RRM1 levels are positively correlated with the DHS cytotoxicity (FIG. 17D), meaning that pancreatic tumor cells with higher RRM1 or RRM2 levels are more sensitive to DHS.

Next, the effect of combined treatment with DHS and gemcitabine on pancreatic tumor cells was investigated. The presence of DHS resensitized the gemcitabine-resistant pancreatic cancer line, RPK-9, to gemcitabine in vitro (FIG. 18A). It also was found that the combination of DHS and gemcitabine demonstrated synergy against resistant cells, with combination indexes (CI) being lower than 1 (FIG. 18B and Tables 8-9). The combination treatment also decreased RRM1 and RRM2 protein levels (FIG. 18C) and triggered cell apoptosis (FIG. 18D). Additionally, a RPK-9 xenograft tumor model demonstrated the therapeutic effect of the combination of DHS and Gemcitabine on tumor growth in vivo (FIG. 19A).

TABLE 8

CI for PK-9 cells treated with DHS and Gem

| Dose DHS (µM) | Dose Gem (µM) | Effect | CI |
|---|---|---|---|
| 10.0 | 1000.0 | 0.03906 | 0.17384 |
| 10.0 | 100.0 | 0.04785 | 0.19027 |
| 10.0 | 10.0 | 0.08203 | 0.2534 |
| 10.0 | 1.0 | 0.10645 | 0.28745 |
| 10.0 | 0.01 | 0.15332 | 0.34527 |
| 10.0 | 0.01 | 0.17676 | 0.37553 |

TABLE 9

CI for RPK-9 cells treated with DHS and Gem

| Dose DHS (µM) | Dose Gem (µM) | Effect | CI |
|---|---|---|---|
| 10.0 | 1000.0 | 0.24919 | 0.24478 |
| 10.0 | 100.0 | 0.57929 | 0.45302 |
| 10.0 | 10.0 | 0.56958 | 0.40867 |
| 10.0 | 1.0 | 0.74110 | 0.71845 |
| 10.0 | 0.1 | 0.69579 | 0.60789 |
| 10.0 | 0.01 | 0.70226 | 0.62185 |

Example 7

DHS Overcomes Cisplatin Resistance in Ovarian Cancer Cells

The effect of DHS on a human SKOV3 ovarian cell line and its cisplatin-resistant subline, SKOV3/CP7, was investigated. The results showed that both SKOV3 and SKOV3/CP7 cell lines were sensitive to DHS treatment alone. DHS also re-sensitized the SKOV3/CP7 cells to cisplatin, and the combination was synergistic given that the overall CI (combinational index) was less than 1 (Table 10).

TABLE 10

CI for SKOV3 and SKOV3-CP7 cells treated with DHS and Cisplatin

| | DHS (µM) | Cisplatin (µM) | CI |
|---|---|---|---|
| SKOV3 | 0.6 | 3.7 | 0.31 |
| | 1.8 | 3.7 | 0.38 |
| | 1.8 | 11.1 | 0.48 |

TABLE 10-continued

CI for SKOV3 and SKOV3-CP7 cells treated with DHS and Cisplatin

|  | DHS (μM) | Cisplatin (μM) | CI |
|---|---|---|---|
|  | 5.6 | 3.7 | 0.50 |
|  | 5.6 | 11.1 | 0.54 |
|  | 16.7 | 11.1 | 0.81 |
| SKOV3-CP7 | 0.6 | 3.7 | 0.27 |
|  | 1.8 | 3.7 | 0.41 |
|  | 1.8 | 11.1 | 0.47 |
|  | 5.6 | 3.7 | 0.44 |
|  | 5.6 | 11.1 | 0.65 |
|  | 16.7 | 11.1 | 0.80 |

Figure 20A:
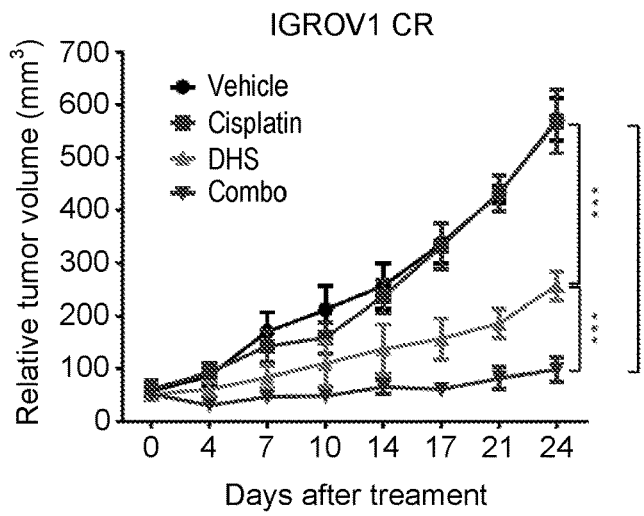
Figure 20B:
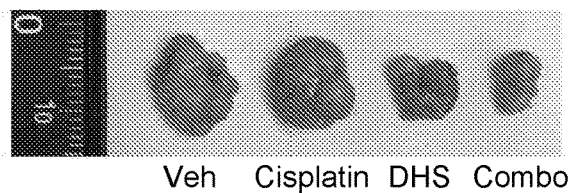
Figure 20C:
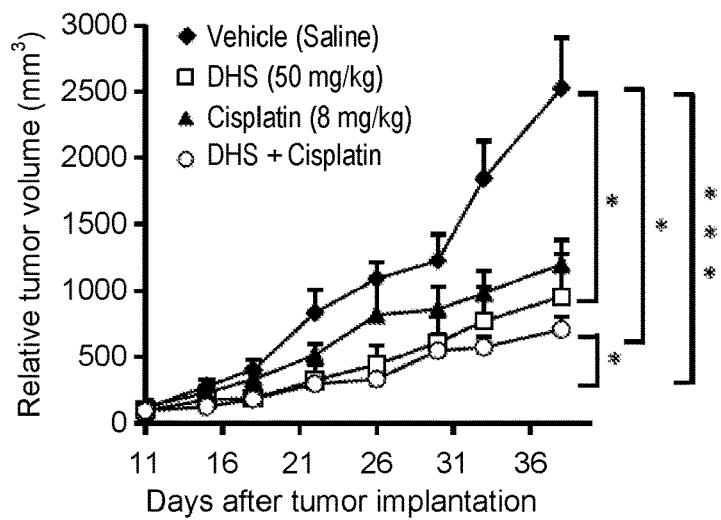
Figure 20D:
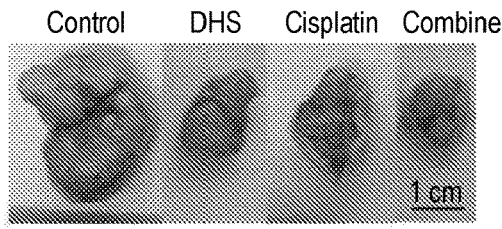
Figure 21A:
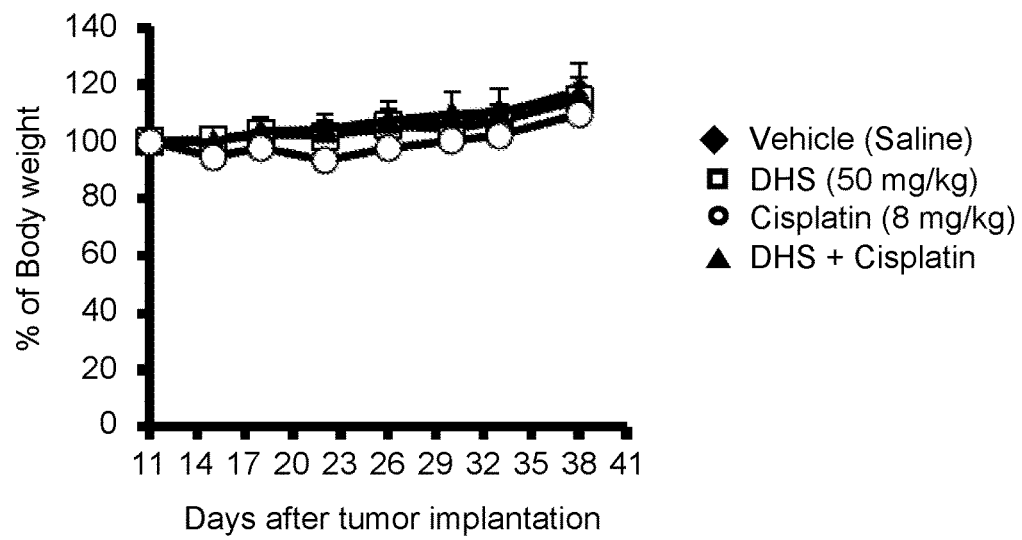
Figure 21B:
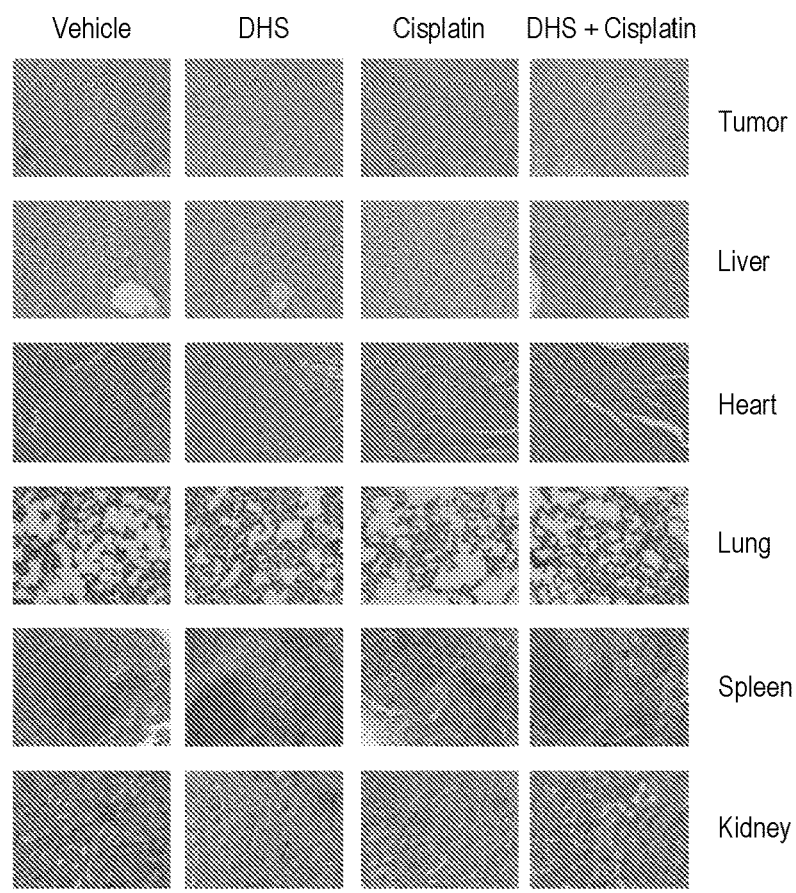

Xenograft tumor models were produced with another cisplatin resistant ovarian cancer cell line, IGROV1 CR. As shown in FIG. 20A, the combination of DHS with cisplatin enhanced the suppression of tumor growth as compared to DHS or cisplatin alone. The therapeutic effect of DHS was further assessed with a HCT116 xenograft tumor model. HCT116 cells ($5 \times 10^6$) were injected subcutaneously in nude mice and grown to approximately 100 mm$^3$ in volume. Treatments with DHS were then conducted at 50 mg/kg in 200 μl for 14 consecutive days by i.p. injection. Cisplatin (8 mg/kg) was given by i.p. injection once a week for two weeks. As compared with the vehicle control group, xenograft tumors that received either DHS or cisplatin grew slower and were smaller (FIG. 20C). On Day 38, groups that received DHS or cisplatin demonstrated about a 50% reduction in tumor volume as compared with the vehicle control group. Combination therapy with DHS and Cisplatin resulted in a further significant reduction in tumor growth as compared to DHS or cisplatin alone (FIG. 20C). Treatment with DHS did not cause any reduction in body weight, suggesting no obvious toxicity (FIG. 21A). To study the preclinical toxicity of DHS, samples of hearts, livers, spleens, lung, and kidneys were collected on Day 38 and sections were stained for histological examination. Minor damage was found in the spleens of groups treated with DHS and cisplatin, alone or in combination. There was no obvious damage to hearts, livers, lung, and kidneys (FIG. 21B).

Collectively, the above results demonstrate a mechanism of action for DHS (FIG. 22), broad-spectrum anti-cancer activities of DHS in vitro and in vivo, and that DHS can resensitize drug-resistant cancer cells to drugs such as cisplatin, gemcitabine, and hydroxyurea and can act synergistically with such drugs.

REFERENCES

Cai, Y. J., et al. (2004). The 3,4-dihydroxyl groups are important for trans-resveratrol analogs to exhibit enhanced antioxidant and apoptotic activities. Anticancer Res 24(2B), 999-1002.

Chen, Z., et al. (2011). Modulation of the ribonucleotide reductase M1-gemcitabine interaction in vivo by N-ethylmaleimide. Biochem Biophys Res Commun 413(2), 383-388.

Chou, T. C. (2006). Theoretical basis, experimental design, and computerized simulation of synergism and antagonism in drug combination studies. Pharmacological Reviews 58, 621-681.

Cory J G and Sato A. (1983). Regulation of ribonucleotide reductase activity in mammalian cells. Mol Cell Biochem 53-54, 257-266.

D'Angiolella, V., et al. (2012). Cyclin F-mediated degradation of ribonucleotide reductase M2 controls genome integrity and DNA repair. Cell 149(5), 1023-34.

Guittet O, Håkansson P, Voevodskaya N, Fridd S, Gräslund A, et al. (2001). Mammalian p53R2 protein forms an active ribonucleotide reductase in vitro with the R1 protein, which is expressed both in resting cells in response to DNA damage and in proliferating cells. J Biol Chem 274, 40637-40651.

Hao, J., de Renty, C., Li, Y., Xiao, H., Kemp, M. G., Han, Z., DePamphilis, M. L., and Zhu, W. (2015). And-1 coordinates with Claspin for efficient Chk1 activation in response to replication stress. The EMBO Journal 34, 2096-2110.

Hosseini, A. and A. Ghorbani (2015). Cancer therapy with phytochemicals: evidence from clinical studies. Avicenna J Phytomed 5(2), 84-97.

Jafari, R., et al. (2014). The cellular thermal shift assay for evaluating drug target interactions in cells. Nat Protoc 9(9), 2100-2122.

Jaramillo-Lambert, A., Hao, J., Xiao, H., Li, Y., Han, Z., and Zhu, W. (2013). Acidic nucleoplasmic DNA-binding protein (And-1) controls chromosome congression by regulating the assembly of centromere protein A (CENP-A) at centromeres. The Journal of Biological Chemistry 288, 1480-1488.

Kohnken, R., K. M. Kodigepalli, and L. Wu (2013). Regulation of deoxynucleotide metabolism in cancer: novel mechanisms and therapeutic implications. Mol Cancer 14, 176.

Li, Y., Jaramillo-Lambert, A. N., Yang, Y., Williams, R., Lee, N. H., and Zhu, W. (2012a). And-1 is required for the stability of histone acetyltransferase Gcn5. Oncogene 31, 643-652.

Li, Y., Xiao, H., de Renty, C., Jaramillo-Lambert, A., Han, Z., DePamphilis, M. L., Brown, K. J., and Zhu, W. (2012b). The involvement of acidic nucleoplasmic DNA-binding protein (And-1) in the regulation of prereplicative complex (pre-RC) assembly in human cells. The Journal of Biological Chemistry 287, 42469-42479.

O'Connor, M. J. (2015). Targeting the DNA Damage Response in Cancer. Molecular Cell 60, 547-560.

Pangeni, R., et al. (2014). Resveratrol: review on therapeutic potential and recent advances in drug delivery. Expert Opin Drug Deliv 11(8), 1285-98.

Plunkett, W., P. Huang, and V. Gandhi (1995). Preclinical characteristics of gemcitabine. Anticancer Drugs 6 Suppl 6, 7-13.

Roos, W. P., Thomas, A. D., and Kaina, B. (2016). DNA damage and the balance between survival and death in cancer biology. Nature Reviews Cancer 16, 20-33.

Sato, N., Koinuma, J., Fujita, M., Hosokawa, M., Ito, T., Tsuchiya, E., Kondo, S., Nakamura, Y., and Daigo, Y. (2010). Activation of WD repeat and high-mobility group box DNA binding protein 1 in pulmonary and esophageal carcinogenesis. Clinical Cancer Research: an official journal of the American Association for Cancer Research 16, 226-239.

Simon, A. C., Zhou, J. C., Perera, R. L., van Deursen, F., Evrin, C., Ivanova, M. E., Kilkenny, M. L., Renault, L., Kjaer, S., Matak-Vinkovic, D., et al. (2014). A Ctf4 trimer couples the CMG helicase to DNA polymerase alpha in the eukaryotic replisome. Nature 510, 293-297.

Thelander, M., A. Graslund, and L. Thelander (1985). Subunit M2 of mammalian ribonucleotide reductase. Characterization of a homogeneous protein isolated from M2-overproducing mouse cells. J Biol Chem 260(5), 2737-2741.

Usha, S., Johnson, I. M., and Malathi, R. (2006). Modulation of DNA intercalation by resveratrol and genistein. Molecular and Cellular Biochemistry 284, 57-64.

van Pel, D. M., Stirling, P. C., Minaker, S. W., Sipahimalani, P., and Hieter, P. (2013). *Saccharomyces cerevisiae* genetics predicts candidate therapeutic genetic interactions at the mammalian replication fork. G3 3, 273-282.

Varoni, E. M., Lo Faro, A. F., Sharifi-Rad, J., and Iriti, M. (2016). Anticancer Molecular Mechanisms of Resveratrol. Frontiers in Nutrition 3, 8.

Vichai, V., and Kirtikara, K. (2006). Sulforhodamine B colorimetric assay for cytotoxicity screening. Nature Protocols 1, 1112-1116.

Zhou, B., et al. (2013). A small-molecule blocking ribonucleotide reductase holoenzyme formation inhibits cancer cell growth and overcomes drug resistance. Cancer Res 73(21), 6484-93.

Having now fully described the methods, compounds, and compositions herein, it will be understood by those of skill in the art that the same can be performed within a wide and equivalent range of conditions, formulations, and other parameters without affecting the scope of the methods, compounds, and compositions provided herein or any embodiment thereof. All patents, patent applications and publications cited herein are fully incorporated by reference herein in their entireties as if each individual publication or patent application were specifically and individually indicated to be incorporated by reference. In addition, citation or identification of any reference in this application shall not be construed as an admission that such reference is available as prior art to the present invention.

What is claimed is:

1. A pharmaceutical composition comprising 4,4'-Trans-dihydroxystilbene (DHS) and a DNA damaging agent.

2. The pharmaceutical composition of claim 1, wherein the DNA damaging agent is selected from the group consisting of a: chemotherapeutic agent, DNA alkylating agent, nucleoside analog, replication inhibitor, platinum-based drug, actinomycin, amsacrine, cyclophosphamide, dactinomycin, daunorubicin, doxorubicin, epirubicin, iphosphamide, merchlorehtamine, mitomycin, mitoxantrone, nitrosourea, procarbazine, taxol, taxotere, teniposide, etoposide, triethylenethiophosphoramide, hydroxyurea, gemcitabine, and any combination thereof.

3. The pharmaceutical composition of claim 1, wherein the DNA damaging agent is gemcitabine.

4. The pharmaceutical composition of claim 1, wherein the DNA damaging agent is hydroxyurea.

5. The pharmaceutical composition of claim 1, wherein the DNA damaging agent is a platinum-based drug.

6. The pharmaceutical composition of claim 5, wherein the platinum-based drug is selected from the group consisting of: cisplatin, carboplatin, diplatinum cytostatic, iproplatin, oxaliplatin, nedaplatin, satraplatin, tetraplatin, and any combination thereof.

7. A kit comprising the pharmaceutical composition of claim 1.

8. A method of treating cancer in a subject, comprising administering to the subject an effective dose of DHS and an effective dose of a DNA damaging agent.

9. The method of claim 8, wherein the DNA damaging agent is administered prior to, concurrently with, or subsequent to DHS.

10. The method of claim 8, wherein the DNA damaging agent is selected from the group consisting of a: chemotherapeutic agent, DNA alkylating agent, nucleoside analog, replication inhibitor, platinum-based drug, actinomycin, amsacrine, cyclophosphamide, dactinomycin, daunorubicin, doxorubicin, epirubicin, iphosphamide, merchlorehtamine, mitomycin, mitoxantrone, nitrosourea, procarbazine, taxol, taxotere, teniposide, etoposide, triethylenethiophosphoramide, hydroxyurea, gemcitabine, and any combination thereof.

11. The method of claim 8, wherein the DNA damaging agent is gemcitabine, hydroxyurea, or a platinum-based drug.

12. The method of claim 11, wherein the platinum-based drug is selected from the group consisting of: cisplatin, carboplatin, diplatinum cytostatic, iproplatin, oxaliplatin, nedaplatin, satraplatin, tetraplatin, and any combination thereof.

13. The method of claim 8, wherein the cancer is selected from the group consisting of: ovarian cancer, testicular cancer, bladder cancer, head and neck cancer, oral cancer, esophageal cancer, lung cancer, small cell lung cancer, non-small cell lung cancer, breast cancer, cervical cancer, stomach cancer, gastric cancer, colorectal cancer, osteosarcoma, pancreatic cancer, prostate cancer, and any combination thereof.

14. A method of treating a disease or disorder in a subject characterized by overexpression of ribonucleotide reductase (RNR) or a subunit thereof, acidic nucleoplasmic DNA-binding protein 1 (And-1), or any combination thereof, comprising administering to the subject an effective dose of DHS and an effective dose of a DNA damaging agent.

15. The method of claim 14, wherein the RNR subunit is ribonucleotide reductase catalytic subunit M1 (RRM1).

16. The method of claim 14, wherein the RNR subunit is ribonucleotide reductase catalytic subunit M2 (RRM2).

17. The method of claim 14, wherein the disease or disorder is a cancer.

18. A method of treating cancer in a subject, comprising administering to the subject an effective dose of DHS, wherein prior to initiation of the method the subject has been identified as having a cancer that is resistant to treatment with at least one DNA damaging agent.

19. A method of decreasing resistance to a DNA damaging agent that is used in the treatment of a disease or disorder in a subject, comprising administering to the subject: a) an effective dose of DHS; and b) an effective dose of a DNA damaging agent.

* * * * *